US009061993B2

(12) United States Patent
MacGregor

(10) Patent No.: US 9,061,993 B2
(45) Date of Patent: Jun. 23, 2015

(54) DERIVATIVES OF PROPANE DIYL DICINNAMATE

(75) Inventor: Alexander MacGregor, Ontario (CA)

(73) Assignee: Toronto Institute of Pharmaceutical Technology, Toronto (CA)

( * ) Notice: Subject to any disclaimer, the term of this patent is extended or adjusted under 35 U.S.C. 154(b) by 1093 days.

(21) Appl. No.: 12/901,113

(22) Filed: Oct. 8, 2010

(65) Prior Publication Data

US 2011/0086912 A1 Apr. 14, 2011

Related U.S. Application Data

(60) Provisional application No. 61/250,287, filed on Oct. 9, 2009.

(51) Int. Cl.
*A61K 31/235* (2006.01)
*C07C 69/734* (2006.01)
(Continued)

(52) U.S. Cl.
CPC .............. *C07C 69/734* (2013.01); *A61K 31/21* (2013.01); *C07C 69/732* (2013.01); *C07D 303/16* (2013.01)

(58) Field of Classification Search
None
See application file for complete search history.

(56) References Cited

U.S. PATENT DOCUMENTS 3,857,873 A 12/1974 Schwender et al.
7,713,556 B2 5/2010 Lowe

FOREIGN PATENT DOCUMENTS

GB 2105190 * 3/1983

OTHER PUBLICATIONS

Database Caplus Chemical Abstracts Service, Columbus, Ohio, US; Database Accession No. 2000:756659, Abstract of WO 200063152, Burke et al., Oct. 26, 2000.*

(Continued)

*Primary Examiner* — Karl J Puttlitz
(74) *Attorney, Agent, or Firm* — Neifeld IP Law

(57) ABSTRACT

The present invention provides a method for treating a cancer in a subject involving administering to the subject a compound of formula (II) or (II'):

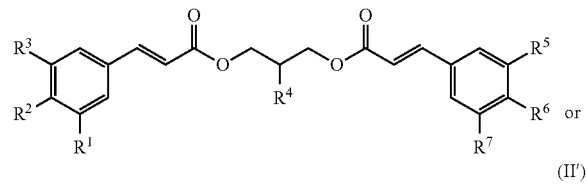

(II)

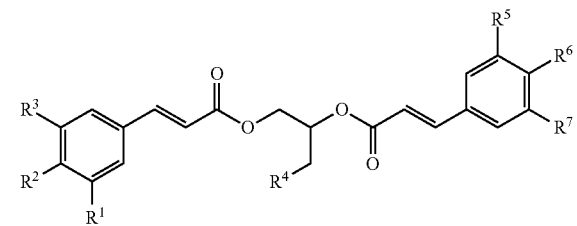

(II')

wherein $R^1$, $R^2$, $R^3$, $R^4$, $R^5$, $R^6$ and $R^7$ are independently H, OH, alkoxy or alkylcarbonyloxy, or a pharmaceutically acceptable salt thereof. Also provided is a compound of formula (II) or (II)', wherein $R^1$ and $R^2$ are independently OH, alkoxy or alkylcarbonyloxy, $R^3$ and $R^4$ are independently H, OH, alkoxy or alkylcarbonyloxy, $R^6$ is H, alkoxy or alkylcarbonyloxy, $R^5$ is H, OH or alkylcarbonyloxy, $R^6$ is H or alkoxy, and $R^7$ is H, or a pharmaceutically acceptable salt thereof.

13 Claims, 15 Drawing Sheets

(51) Int. Cl.
    *A61K 31/21* (2006.01)
    *C07C 69/732* (2006.01)
    *C07D 303/16* (2006.01)

(56) References Cited

OTHER PUBLICATIONS

Von Roen, Treatment of HIV-Associated Kaposi Sarcoma, 2003, HIV Insite at <http://hivinsite.ucsf.edu/InSite?page=kb-00&doc=kb-06-02-04>>, visited Jan. 6, 2014.*
Jang et al., J. Agric. Food Chem. 2004, 52, 2218-2222.*
Howe et al., Breast Cancer Research 2007, 9:210.*
Queiroga M. A. et al, Chemical constituents from *Tillandsia recurvata*, 75 (2004) 423-425, Fitoterapia (Elsevier), Amsterdam.
Wright, James S., Predicting the antioxidant activity of curcumin and curcuminoids, Journal of Molecular Structure (Theochem) 591 (2002) 207-217, Elsevier, Amsterdam.
Michael Sefkow et al., "Selective Protection of Either the Phenol or the Hydroxy Group in Hydroxyalkyl Phenols", *Science Direct*, Tetrahedron Letters, vol. 40, Issue 36, Sep. 3, 1999, pp. 6561-6562.
Young-Sik Jung et al., "Convenient synthesis of 3,5-dialkoxy-4-hydroxy cinnamic acids", J. Appl. Biomed. 5: 13-17, 2007, ISSN 1214-0287.
Harry W. Gibson et al., "Regioselective routes to disubstituted dibenzo crown ethers and their complexations", Org. Biomol. Chem., 2005, 3, 2114-2121.
Ming-Chung Jiang et al., "Curcumin Induces Apoptosis in Immortalized NIH 3T3 and Malignant Cancer Cell Lines", Nutr Cancer 26: 111-120, 1996.
Min-Liang Kuo et al., "Curcumin, an antioxidant and anti-tumor promoter, induces apoptosis in human leukemia cells", Biochimica et Biophysica Acta 1317: (1996) 95-100.
Kapil Mehta et al., "Antiproliferative effect of curcumin (diferuloylmethane) against human breast tumor cell lines", Anti-Cancer Drugs 1997 8: 470-481.
Hanan S. Samaha et al. "Modulation of Apoptosis by Sulindac, Curcumin, Phenylethyl-3-methylcaffeate, and 6-Phenylhexyl Isothiocyanate: Apoptotic Index as a Biomarker in Colon Cancer Chemoprevention and promotion", Cancer Res 57: 1301-1305, 1997.
A. Simon et al., "Inhibitory effect of curcuminoids on MCF-7 cell proliferation and structure-activity relationships", Cancer Letters 129 (1998) 111-116.
Shiou-Hwa Jee et al., "Curcumin Induces a p53-Dependent Apoptosis in Human Basal Cell Carcinoma Cells", The Society for Investigative Dermatology, vol. 111, No. 4, Oct. 1998, 656-661, 1998.
Asok Mukhopadhyay et al., "Curcumin downregulates cell survival mechanisms in human prostate cancer cell lines", Oncogene (2001), 20, 7597-7609.
D. Grunberger et al., "Preferential cytotoxicity on tumor cells by caffeic acid phenethyl ester isolated from propolis". Experientia 44: (1988), 230-232.
Zao-zhong Su et al. "Suppression of Adenovirus Type 5 E1A-Mediated Transformation and Expression of the Transformed Phenotype by Caffeic Acid Phenethyl Ester (CAPE)", Molecular Carcinogenesis 4: 1991, 231-242.
Ludovico Guarini et al., Growth Inhibition and Modulation of Antigenic Phenotype in Human Melanoma and Glioblastoma Multiforme Cells by Caffeic Acid Phenethyl Ester (CAPE), Cellular Molecular Biology 38 (5), 1992, 513-527.
Chinthalapally V. Rao et al., "Effect of Caffeic Acid Esters on Carcinogen-Induced Mutagenicity and Human Colon Adenocarcinoma Cell Growth", Chem. Biol. Interactions, 84, (1992) 277-290.
Chinthalapally V. Rao et al., "Inhibitory Effect of Caffeic Acid Esters on Azoxymethane-induced Biochemical Changes and Aberrant Crypt Foci Formation in Rat Colon", Cancer Research 53, Sep. 15, 1993, 4182-4188.
Krystyna Frenkel et al., "Inhibition of Tumor Promoter-mediated processes in Mouse Skin and Bovine Lens by Caffeic acid Phenethyl Ester", Cancer Research 53, Mar. 15, 1993,1255-1261.
Dae Sik Jang et al., "Constituents of *Asparagus officinalis* Evaluated for Inhibitory Activity against Cyclooxygenase-2", Journal of Agricultural and Food Chemistry, 2004, vol. 52, 2218-2222.
Feng Li et al., "Study on the Constituents of Mexican Propolis and Their Cytotoxic Activity against PANC-1 Human Pancreatic Cancer Cells", J. Nat. Prod., (published on the Web Mar. 22, 2010, vol. 73, 623-627.
Aurelio De Queiroga, M et al., "Chemical constituents from *Tillandsia recurvata*", Fitoterapia, vol. 75 2004, 423-425.
Rao, et al., "Chemoprevention of Colon Carcinogenesis by Dietary Curcumin, a Naturally Occurring Plant Phenolic Compound", Cancer Research vol. 55, 1995, 259-266.
Banskota, Arjun H., et al., "Antiproliferative activity of the Netherlands propolis and its active principles in cancer cell lines," Journal of Ethnopharmacology 80, 2002, pp. 67-73.

* cited by examiner

DERIVATIVES OF PROPANE DIYL DICINNAMATE

FIELD OF INVENTION

The present invention relates to therapeutic agents for treating cancer. More particularly, the present invention relates to propane diyl dicinnamate derivatives for treating cancer and methods for their preparation.

BACKGROUND OF INVENTION

According to the World health Organization, malignant tumours were responsible for 12 percent of the nearly 56 million deaths worldwide from all causes in the year 2000. In particular, 5.3 million men and 4.7 million women developed a malignant tumour and altogether 6.2 million died from the disease. The report also reveals that cancer has emerged as a major public health problem in developing countries, matching its effect in industrialized nations.

Although substantial progress has been made in the past two decades, there remain many cancers for which conventional therapy are either partially or totally ineffective. The main common problem with these therapies is unacceptable toxicity.

Thus, novel compounds, agents or methods are needed either to prevent the development of cancer, or, in the case where neoplasia has already developed, to render the host organism cancer-free or to reduce its neoplastic burden to a level compatible with life or at least to facilitate the use of concomitant therapies.

In its essence, neoplasia, including cancer, can be regarded as the inappropriate accumulation of cells, in violation of the delicate balance between cell renewal and cell death. For neoplasia to develop, either cell renewal must be increased or cell death decreased or both. A corollary to this relationship is that an agent that affects these processes favorably for the host organism (and, consequently, unfavorably for the neoplasm), is a potential antineoplastic drug.

Several antineoplastic agents have been isolated and identified from natural sources. For example, Curcumin (diferuloylmethane), a polyphenol derived from the plant *Curcuma longa*, commonly called turmeric has been extensively studied over the last 50 years and these studies indicate that this polyphenol can both prevent and treat cancer. More specifically, these series of studies have shown that Curcumin suppresses the proliferation of a wide variety of tumor cells, including breast carcinoma, colon carcinoma, acute myelogenous leukemia, basal cell carcinoma, melanoma and prostate carcinoma.(1-7) Despite the remarkable pharmacological safety profile of this compound, its effectiveness as a plausible anticancer agent has been limited by poor systemic absorption and extensive metabolism with administered doses.

A specific component of the honeybee hive product propolis, identified as caffeic acid phenyl ester (CAPE), has been shown to selectively inhibit the growth of viral-transformed and oncogene-transformed rodent cells as well as human tumor cells, including glioblastoma multiforme (GBM-18), colon adenocarcinoma (HT-29), and melanoma (HO-1) cells. These studies also show that CAPE and several additional caffeic acid esters inhibit azoxymethane-induced colonie preneoplastic lesions and ornithine decarboxylase, tyrosine protein kinase, and lipoxygenase activities associated with colon carcinogenesis.(8-13)

Although derived from different natural sources, CAPE and the Curcuminoids possess structural similarity that may likely explain their anticancer properties or at least partially explain their safety and selectivity profile. The significance of this structural similarity with regard to their anticancer properties is currently unknown.

An approach for developing new antineoplastic agents is to synthesize novel chemical compounds that are selective for cancer, stable in the biological milieu, maintain potency against cancer and exhibit low toxicity overall.

Banskota et al. (*Journal of Ethnopharmacology* (2002), 80(1), 67-73) isolated the cinnamic acid derivatives benzyl caffeate, phenethyl caffeate and cinnamyl caffeate, as well as the dicinnamate compounds (2E,2'E)-2-acetoxypropane-1,3-diyl bis(3-(4-hydroxyphenyl)acrylate) and (E)-2-acetoxy-3-(((E)-3-(4-hydroxy-3-methoxyphenyl)acryloyl)oxy)propyl 3-(4-hydroxyphenyl)acrylate from a MeOH extract of Netherlands propolis. Benzyl caffeate, phenethyl caffeate and cinnamyl caffeate displayed $EC_{50}$ values of 2.03 µM, 3.16 µM and 1.92 µM, respectively, against B16-BL6. The dicinnamate compounds (2E,2'E)-2-acetoxypropane-1,3-diyl bis (3-(4-hydroxyphenyl)acrylate) and (E)-2-acetoxy-3-(((E)-3-(4-hydroxy-3-methoxyphenyl)acryloyl)oxy)propyl 3-(4-hydroxyphenyl)acrylate displayed moderate $EC_{50}$ values of 81.9 µM and 66 µM, respectively, against the same cell line.

SUMMARY OF INVENTION

The present invention relates to therapeutic agents for treating cancer. More particularly, the present invention relates to propane diyl dicinnamate derivatives for treating cancer and methods for their preparation.

In one aspect, the present invention provides a compound of formula (I) or (I'):

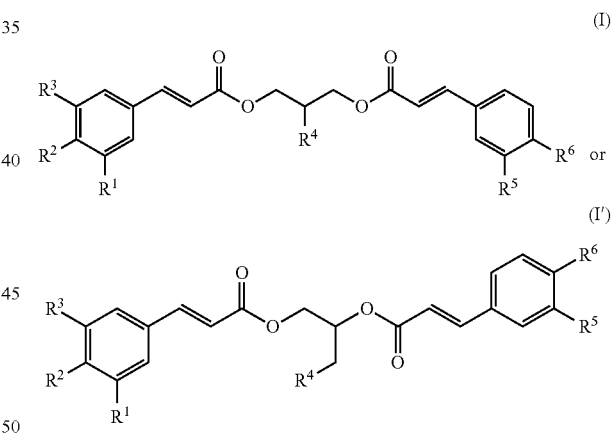

wherein:
$R^1$ and $R^2$ are independently OH, alkoxy or alkylcarbonyloxy,
$R^3$ and $R^4$ are independently H, OH, alkoxy or alkylcarbonyloxy, and
$R^5$ is H, OH or alkylcarbonyloxy, and
$R^6$ is H or alkoxy,
or a pharmaceutically acceptable salt thereof,
provided that the compound is not
(E)-2-acetoxy-3-(((E)-3-(3,4-dimethoxyphenyl)acryloyl) oxy)propyl 3-(4-methoxyphenyl)acrylate or
(E)-3-(((E)-3-(3,4-dimethoxyphenyl)acryloyl)oxy)-2-hydroxypropyl 3-(4-methoxyphenyl)acrylate.

In another aspect, the present invention provides a method for treating a cancer in a subject, comprising administering to the subject a compound of formula (II) or (II'):

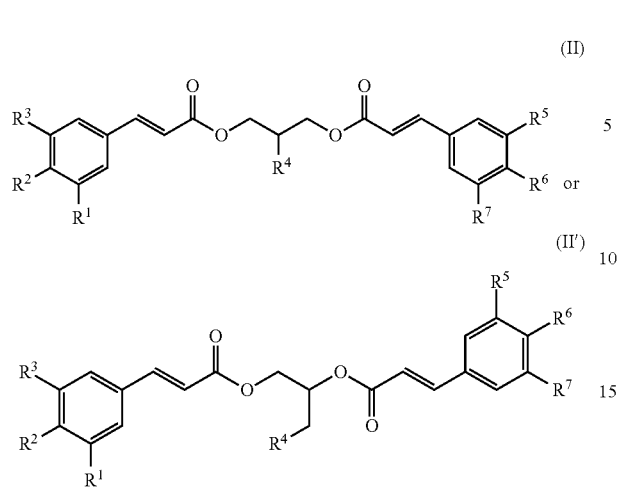

(II)

(II')

wherein $R^1$, $R^2$, $R^3$, $R^4$, $R^5$, $R^6$ and $R^7$ are independently H, OH, alkoxy or alkylcarbonyloxy, or a pharmaceutically acceptable salt thereof, provided that the compound is other than (2E,2'E)-2-acetoxypropane-1,3-diyl bis(3-(4-hydroxyphenyl)acrylate) and (E)-2-acetoxy-3-(((E)-3-(4-hydroxy-3-methoxyphenyl)acryloyl)oxy)propyl 3-(4-hydroxyphenyl)acrylate.

In a further aspect, the present invention provides an intermediate of the formula:

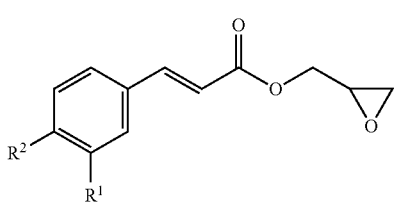

wherein $R^1$ and $R^2$ are both alkoxy.

BRIEF DESCRIPTION OF THE DRAWINGS

These and other features of the invention will become more apparent from the following description in which reference is made to the appended drawings wherein.

DETAILED DESCRIPTION OF INVENTION

Figure 1:
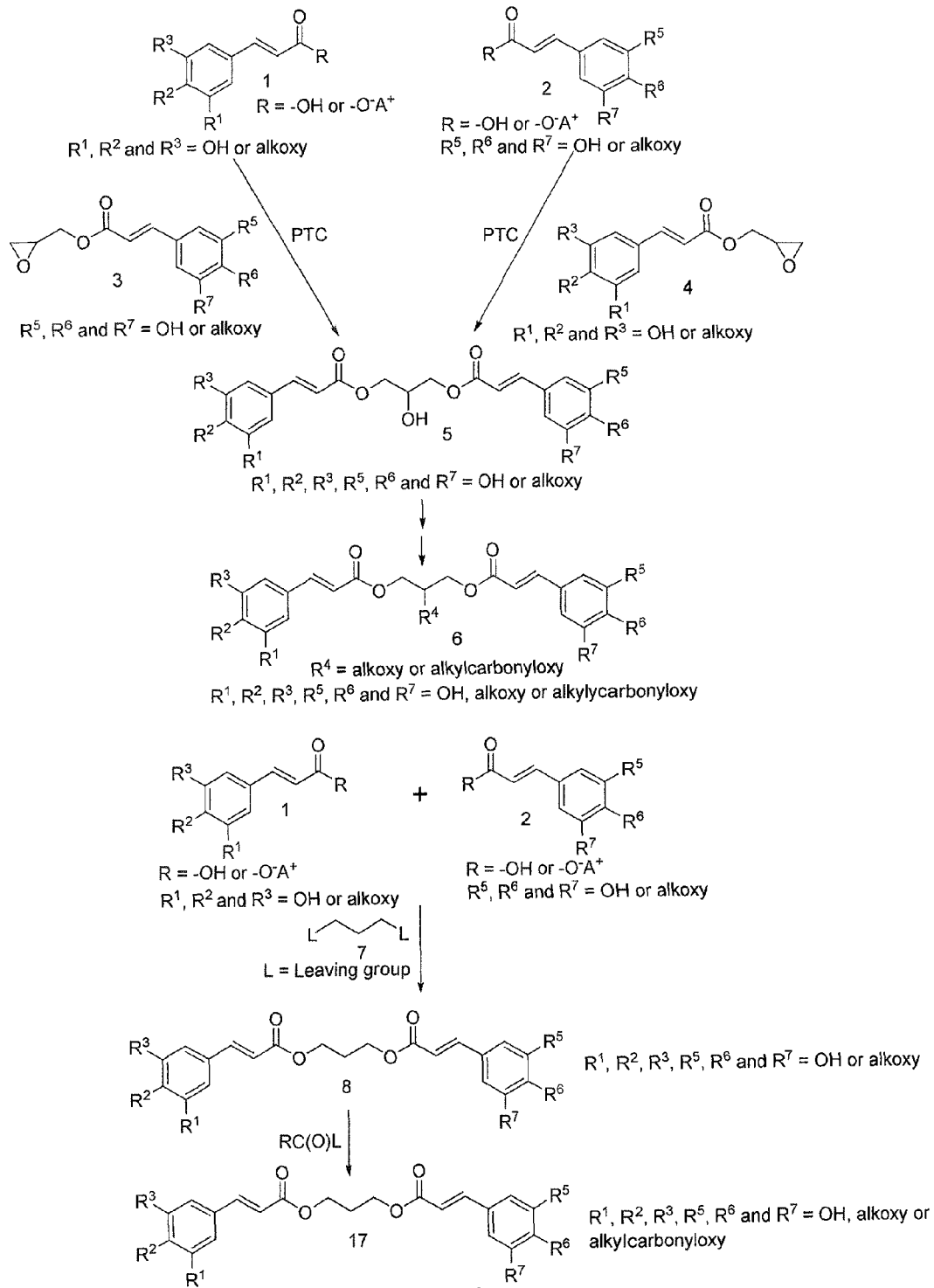
FIGS. 1 and 9-11 illustrate examples of synthetic schemes for producing diester compounds of formula (II).

The present invention relates to therapeutic agents for treating cancer. More particularly, the present invention relates to propane diyl dicinnamate derivatives for treating cancer and methods for their preparation.

In a first aspect, the present invention provides a compound of formula (I) or (I'):

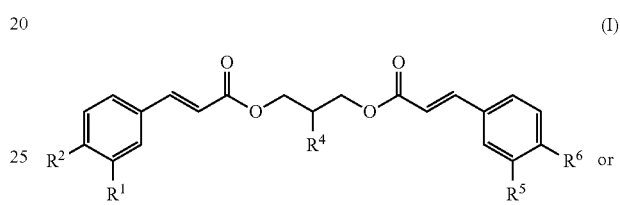

(I)

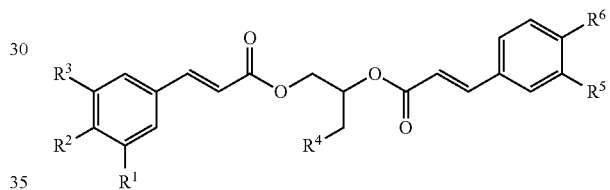

(I')

wherein:

$R^1$ and $R^2$ are independently OH, alkoxy or alkylcarbonyloxy, $R^3$ and $R^4$ are independently H, OH, alkoxy or alkylcarbonyloxy, and $R^5$ is H, OH or alkylcarbonyloxy, and $R^6$ is H or alkoxy, or a pharmaceutically acceptable salt thereof, provided that the compound is not (E)-2-acetoxy-3-(((E)-3-(3,4-dimethoxyphenyl)acryloyl)oxy)propyl 3-(4-methoxyphenyl)acrylate, or (E)-3-(((E)-3-(3,4-dimethoxyphenyl)acryloyl)oxy)-2-hydroxypropyl 3-(4-methoxyphenyl)acrylate.

In an example of the above-defined compound formula (I) or (I'), both $R^1$ and $R^2$ are OH, alkoxy or alkylcarbonyloxy.

More particularly, the present invention provides a compound of formula (Ia) or (Ia'):

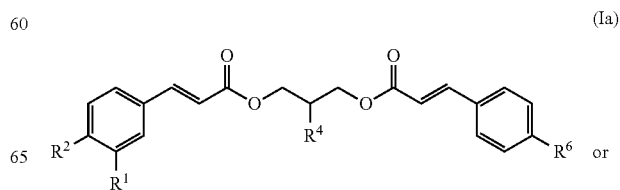

(Ia)

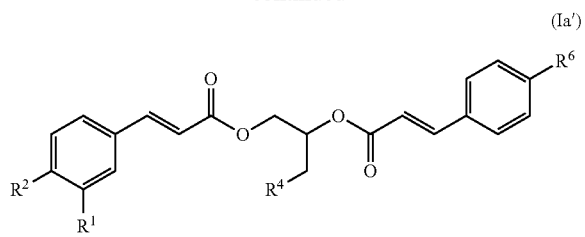

wherein:
R¹ and R² are independently OH, alkoxy or alkylcarbonyloxy,
R⁴ is H, OH, alkoxy or alkylcarbonyloxy, and
R⁶ is H or alkoxy,
or a pharmaceutically acceptable salt thereof,
provided that the compound is not
(E)-2-acetoxy-3-(((E)-3-(3,4-dimethoxyphenyl)acryloyl)oxy)propyl 3-(4-methoxyphenyl)acrylate or
(E)-3-(((E)-3-(3,4-dimethoxyphenyl)acryloyl)oxy)-2-hydroxypropyl 3-(4-methoxyphenyl)acrylate.

In an example of the above-defined compound of formula (Ia) or (Ia'), both R¹ and R² are OH, alkoxy or alkylcarbonyloxy.

In other examples, the present invention relates to the compounds of formulas (I), (Ia), (I') and (Ia') described above, wherein R¹ and R² are both OH or both alkoxy.

The present invention also relates to the above-defined compounds of formulas (I), (Ia), (I') and (Ia'), wherein R⁴ is H or OH.

The present invention also relates to a compound of the formula (Ib) or (Ib'):

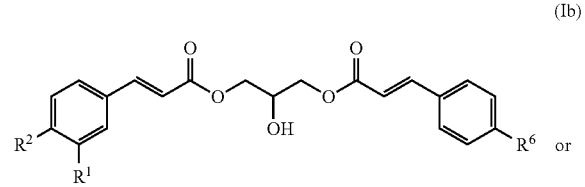

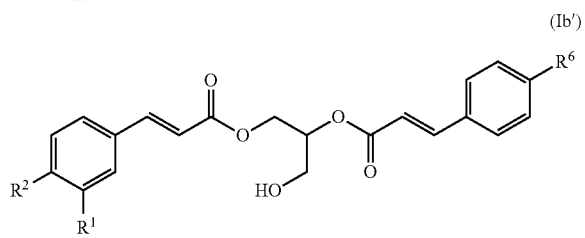

wherein:
R¹ and R² are independently OH, alkoxy or alkylcarbonyloxy, and
R⁶ is H or alkoxy,
or a pharmaceutically acceptable salt thereof,
provided that the compound is not
(E)-3-(((E)-3-(3,4-dimethoxyphenyl)acryloyl)oxy)-2-hydroxypropyl 3-(4-methoxyphenyl)acrylate.

In another example, the present invention relates to a compound of formula (Ic) or (Ic'):

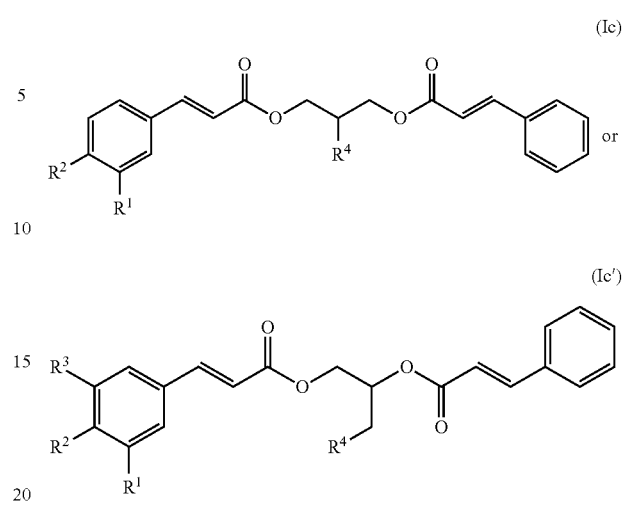

wherein:
R¹ and R² are independently OH, alkoxy or alkylcarbonyloxy, and
R⁴ is H, OH, alkoxy or alkylcarbonyloxy,
or a pharmaceutically acceptable salt thereof.

More particularly, the present invention relates to a compound of the formula (Id), (Ie), (If), (Ig), (Ih), (Ii), (Ij), (Id'), (Ie'), (If'), (Ig'), (Ih'), (Ii'), (Ij'):

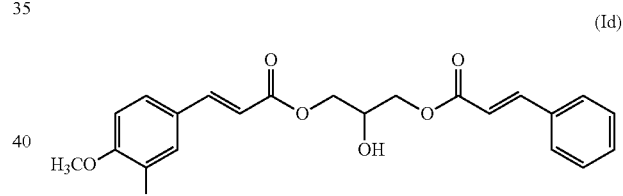

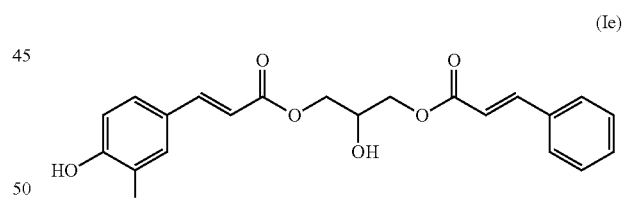

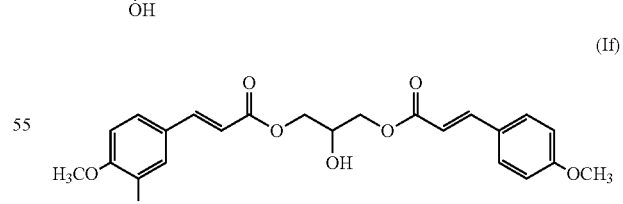

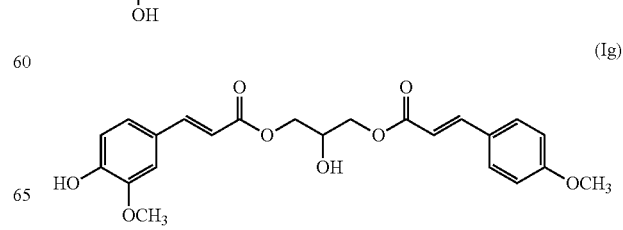

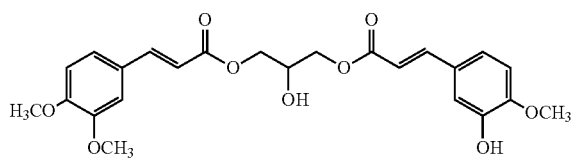 (Ih)

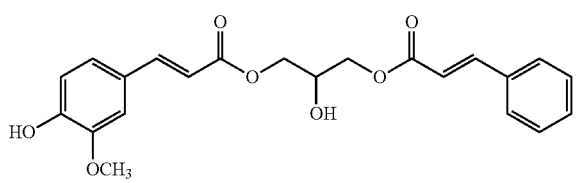 (Ii)

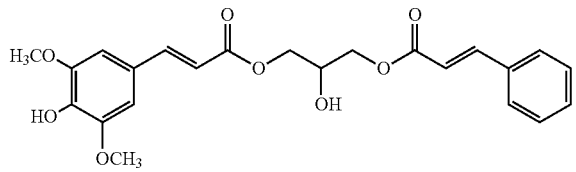 (Ij)

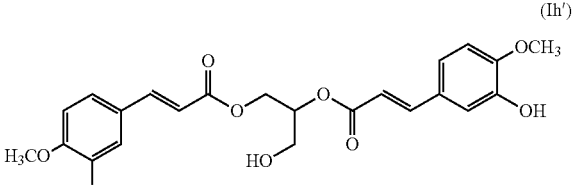 (Ih′)

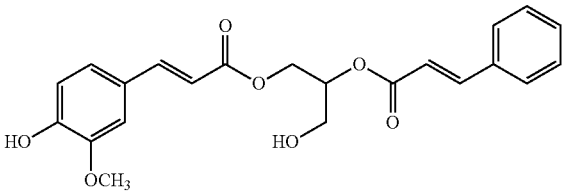 (Ii′)

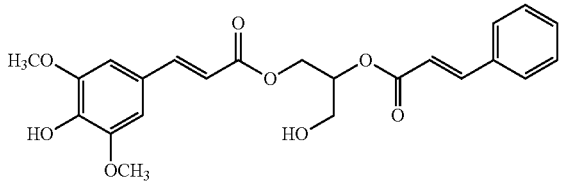 (Ij′)

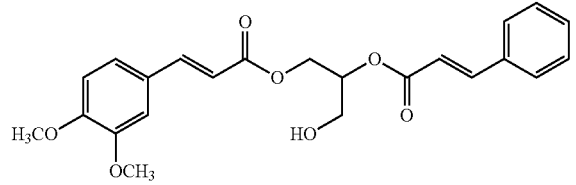 (Id′)

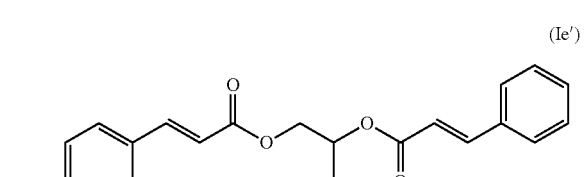 (Ie′)

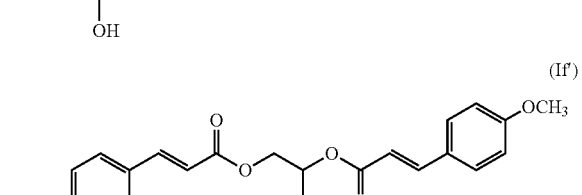 (If′)

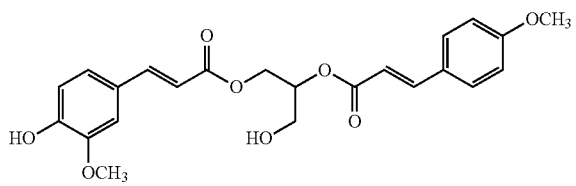 (Ig′)

In a second aspect, the present invention provides a method for treating a cancer, such as lung cancer, breast cancer, colon cancer, prostate cancer, ovarian cancer, skin cancer or leukemia in a subject, comprising administering to the subject a compound of formula (II) or (II′):

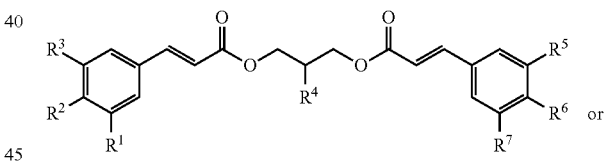 (II)

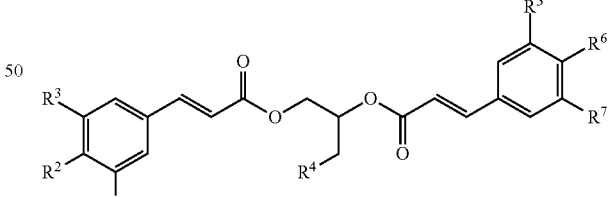 (II′)

wherein $R^1$, $R^2$, $R^3$, $R^4$, $R^5$, $R^6$ and $R^7$ are independently H, OH, alkoxy or alkylcarbonyloxy, or a pharmaceutically acceptable salt thereof, provided that the compound is other than (2E,2′E)-2-acetoxypropane-1,3-diyl bis(3-(4-hydroxyphenyl)acrylate) and (E)-2-acetoxy-3-(((E)-3-(4-hydroxy-3-methoxyphenyl)acryloyl)oxy)propyl 3-(4-hydroxyphenyl)acrylate.

In a third aspect, the present invention provides a use of a compound of formula (II) or (II′):

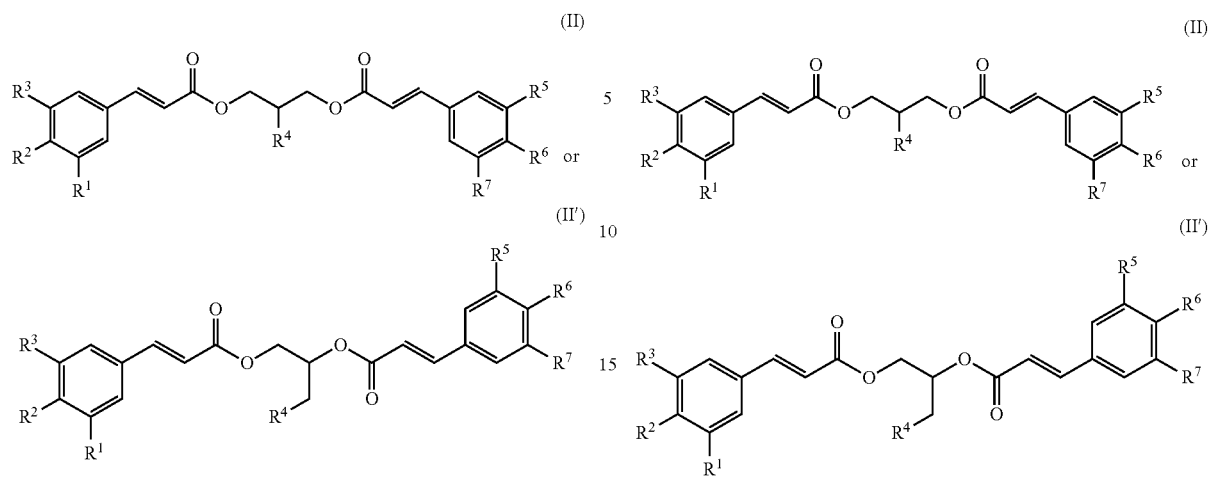

wherein $R^1$, $R^2$, $R^3$, $R^4$, $R^5$, $R^6$ and $R^7$ are independently H, OH, alkoxy or alkylcarbonyloxy, or a pharmaceutically acceptable salt thereof, provided that the compound is other than (2E,2'E)-2-acetoxypropane-1,3-diylbis(3-(4-hydroxyphenyl)acrylate) and (E)-2-acetoxy-3-(((E)-3-(4-hydroxy-3-methoxyphenyl)acryloyl)oxy)propyl 3-(4-hydroxyphenyl)acrylate, for preparing a medicament for treating cancer in a subject.

In an example of the use according to the third aspect of the present invention, the cancer is lung cancer, breast cancer, colon cancer, prostate cancer, ovarian cancer, skin cancer or leukemia.

In a fourth aspect, the present invention provides a method for killing cancer cells, such as lung cancer cells, breast cancer cells, colon cancer cells, prostate cancer cells, ovarian cancer cells, skin cancer cells or leukemia cells, comprising contacting the cancer cells with a compound of formula (II) or (II'):

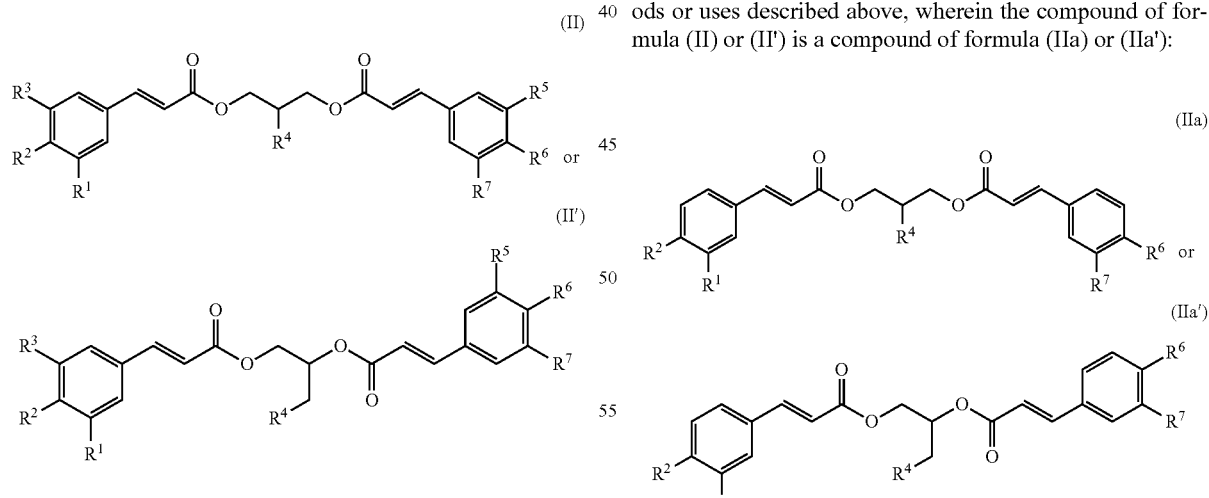

wherein $R^1$, $R^2$, $R^3$, $R^4$, $R^5$, $R^6$ and $R^7$ are independently H, OH, alkoxy or alkylcarbonyloxy, or a pharmaceutically acceptable salt thereof, provided that the compound is other than (2E,2'E)-2-acetoxypropane-1,3-diyl bis(3-(4-hydroxyphenyl)acrylate) and (E)-2-acetoxy-3-(((E)-3-(4-hydroxy-3-methoxyphenyl)acryloyl)oxy)propyl 3-(4-hydroxyphenyl)acrylate.

In a fifth aspect, the present invention provides a use of a compound of formula (II) or (II'):

wherein $R^1$, $R^2$, $R^3$, $R^4$, $R^5$, $R^6$ and $R^7$ are independently H, OH, alkoxy or alkylcarbonyloxy, or a pharmaceutically acceptable salt thereof, provided that the compound is other than (2E,2'E)-2-acetoxypropane-1,3-diyl bis(3-(4-hydroxyphenyl)acrylate) and (E)-2-acetoxy-3-(((E)-3-(4-hydroxy-3-methoxyphenyl)acryloyl)oxy)propyl 3-(4-hydroxyphenyl)acrylate, for killing cancer cells.

In an example of the use according to the fifth aspect of the present invention, the cancer cells are lung cancer cells, breast cancer cells, colon cancer cells, prostate cancer cells, ovarian cancer cells, skin cancer cells or leukemia cells.

In an example of the above-defined methods or uses, both $R^1$ and $R^2$ in the compound of formula (II) or (II') are OH, alkoxy or alkylcarbonyloxy.

More particularly, the present invention relates to the methods or uses described above, wherein the compound of formula (II) or (II') is a compound of formula (IIa) or (IIa'):

wherein $R^1$, $R^2$, $R^4$, $R^6$ and $R^7$ are independently H, OH, alkoxy or alkylcarbonyloxy, or a pharmaceutically acceptable salt thereof.

The present invention relates to the methods or uses described above, wherein the compound of formula (II) or (II') is a compound of formula (Ia) or (Ia'):

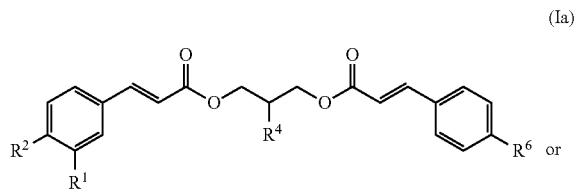
(Ia)

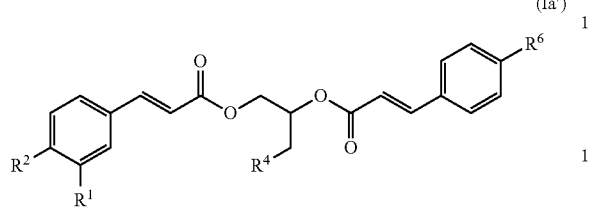
(Ia')

wherein:
$R^1$ and $R^2$ are independently OH, alkoxy or alkylcarbonyloxy,
$R^4$ is H, OH, alkoxy or alkylcarbonyloxy, and
$R^6$ is H or alkoxy,
or a pharmaceutically acceptable salt thereof.

The present invention further relates to the methods or uses described above, wherein the compound of formula (II) or (II') is a compound of formula (Ic) or (Ic'):

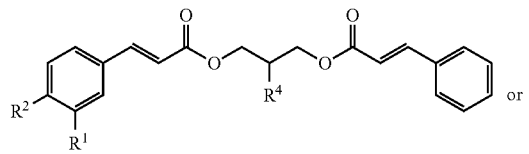
(Ic)

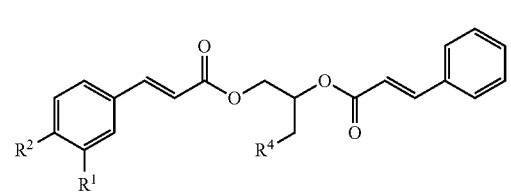
(Ic')

wherein:
$R^1$ and $R^2$ are independently OH, alkoxy or alkylcarbonyloxy, and
$R^4$ is H, OH, alkoxy or alkylcarbonyloxy,
or a pharmaceutically acceptable salt thereof.

In an example of the above-defined methods or uses, $R^1$ and $R^2$ in formulas (II), (IIa), (Ia), (Ic), (II'), (IIa'), (Ia') and (Ic') are both OH, alkoxy or alkylcarbonyloxy.

In other examples, the present invention relates to the above-defined methods or uses, wherein $R^1$ and $R^2$ in formulas (II), (IIa), (Ia), (Ic), (II'), (IIa'), (Ia') and (Ic') are both OH or both alkoxy.

The present invention also relates to the above-defined methods or uses, wherein $R^4$ in formulas (II), (IIa), (Ia), (Ic), (II'), (IIa'), (Ia') and (Ic') is H or OH.

More particularly, the present invention relates to the methods or uses defined above, wherein the compound administered to the subject is of the formula (Id), (Ie), (If), (Ig), (IIb), (IIc), (IId), (IIe), (Id'), (Ie'), (If'), (Ig'), (IIb'), (IIe), (IId'), (IIe') or a combination thereof:

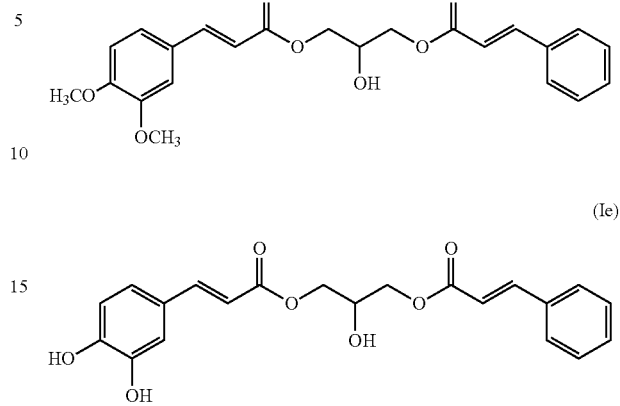
(Id)

(Ie)

(If)

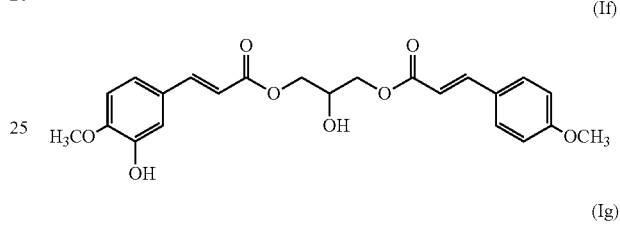
(Ig)

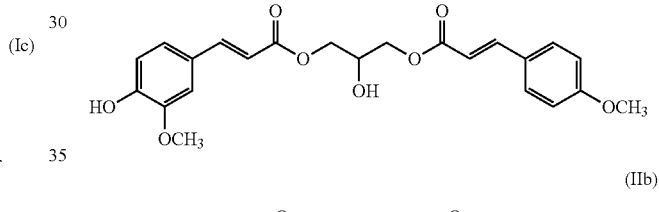
(IIb)

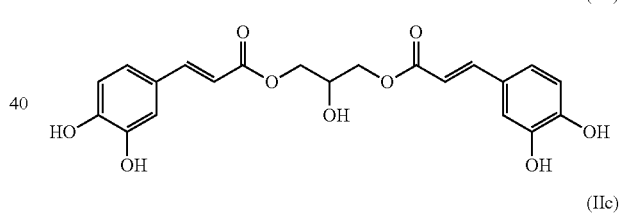
(IIc)

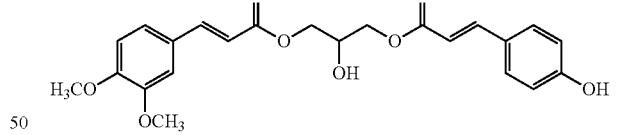
(IId)

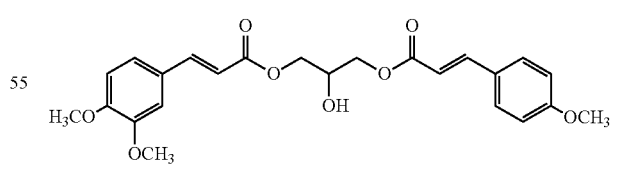
(IIe)

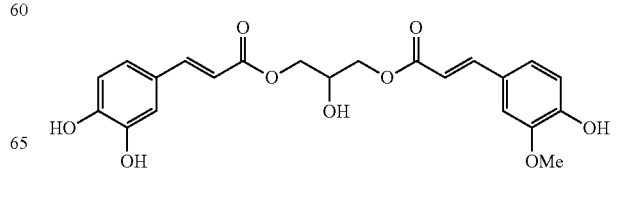

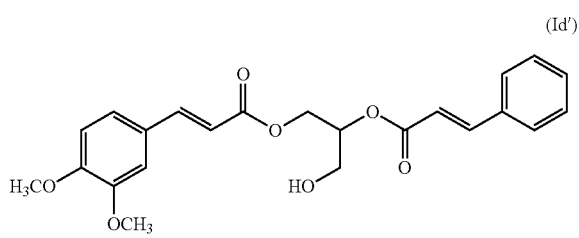
(Id')

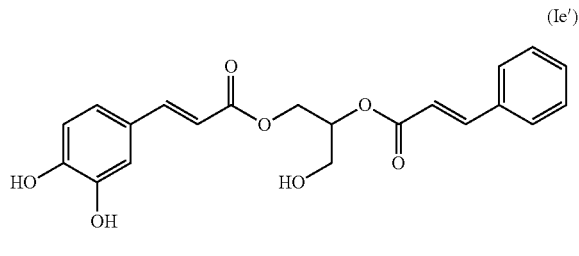
(Ie')

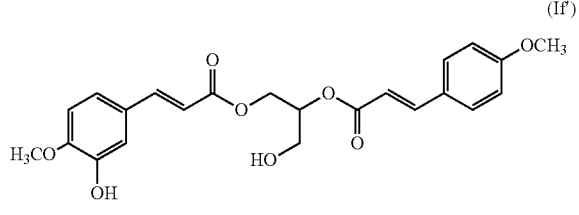
(If')

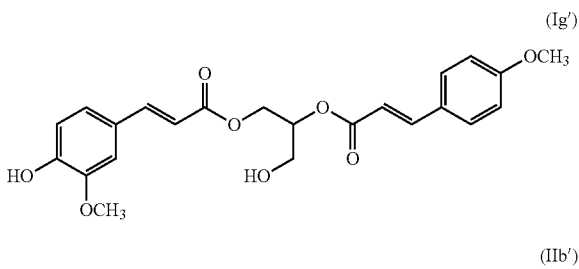
(Ig')

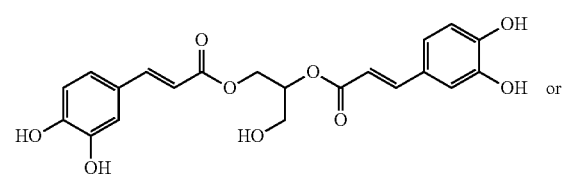
(IIb')

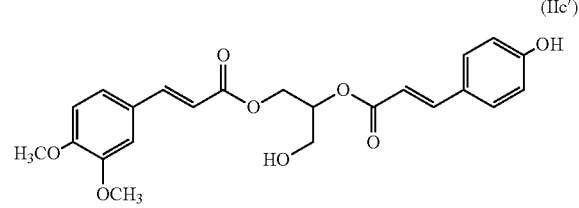
(IIc')

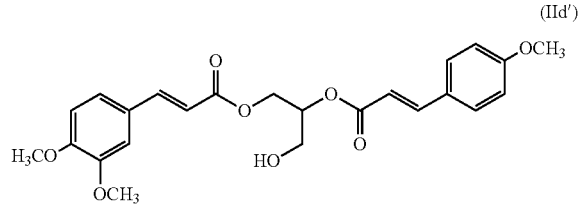
(IId')

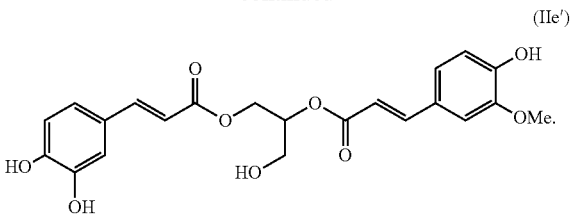
(IIe')

In a sixth aspect, the present invention provides a pharmaceutical composition comprising:

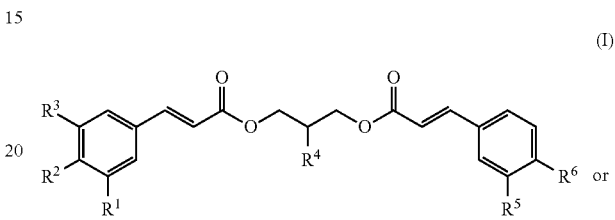
(I)

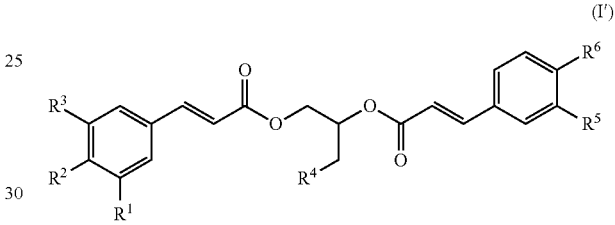
(I')

wherein:
$R^1$ and $R^2$ are independently OH, alkoxy or alkylcarbonyloxy,
$R^3$ and $R^4$ are independently H, OH, alkoxy or alkylcarbonyloxy, and
$R^5$ is H, OH or alkylcarbonyloxy, and
$R^6$ is H or alkoxy,
or a pharmaceutically acceptable salt thereof, and
a pharmaceutically acceptable diluent or carrier,
provided that the compound is not
(E)-2-acetoxy-3-(((E)-3-(3,4-dimethoxyphenyl)acryloyl)oxy)propyl 3-(4-methoxyphenyl)acrylate, or
(E)-3-(((E)-3-(3,4-dimethoxyphenyl)acryloyl)oxy)-2-hydroxypropyl 3-(4-methoxyphenyl)acrylate.

In a seventh aspect, the present invention provides an intermediate of the formula:

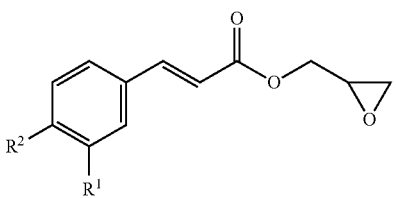

wherein $R^1$ and $R^2$ are both alkoxy.

The present application also relates to a method of treating cancer in a subject, comprising administering to the subject a compound of formula The present invention also relates to a pharmaceutical composition comprising the compound defined above, and a pharmaceutically acceptable diluent or carrier.

The present invention also relates to pharmaceutical compositions and dosage forms comprising compounds of the general formulas (I), (I'), (II) and (II') or mixtures thereof.

As used herein, the term "alkyl" refers to a straight- or branched-chain hydrocarbon radical of the general formula $C_nH_{2n+1}$, such as an alkyl group having 1 to 10, 1 to 9, 1 to 8, 1 to 7, 1 to 6, 1 to 5, 1 to 4, 1 to 3 or 1 to 2 carbon atoms. Examples of alkyl groups include, but are not limited to, methyl, ethyl, propyl, isopropyl, and t-butyl.

The term "pharmaceutically acceptable salt" refers to a salt that retains the biological effectiveness and properties of a corresponding free base or free acid, and which is not biologically or otherwise undesirable. The salt may be prepared from addition of an inorganic base or an organic base to a free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, or a polymine resin.

The compounds of the present invention or their corresponding pharmaceutically acceptable salts can be used in the form of pharmaceutical compositions for enteral, parenteral or topical administration. They can be administered, for example, perorally, e.g. in the form of tablets, coated tablets, dragees, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragees and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

The propane diyl dicinnamate derivatives represented by the general formulas (I), (I'), (II) and (II') defined above are useful for treatment, prophylaxis and prevention of cancers and other proliferative diseases including, but not limited to, tumors, inflammation and human immunodeficiency (HIV). The anticancer activity exhibited by the compounds of the present invention may be through cytotoxicity, antiproliferation, cell cycle kinase inhibition or through cell differentiation.

The present invention also relates to processes for the preparation of compounds defined by the general formulas (I), (I'), (II) and (II') or mixtures thereof, their stereoisomers, their polymorphs, their pharmaceutical acceptable salts, and their pharmaceutically acceptable solvates.

The compounds of general formula (II) can be formed according to the synthetic pathways outlined in FIGS. 1 and 9-11. Referring specifically to FIG. 1, 1,3 glycerol diester 5 (formula (II), $R^4$=OH) can be formed by allowing cinnamic acid derivative 1 or 2 to react with the corresponding glycidyl cinnamate derivative 3 or 4 in the presence of a phase transfer catalyst (PTC). Diester 5 can be further alkylated or acylated to produce derivatized diester 6.

Compounds of formula (II), where $R^4$ is hydrogen, can be formed by crosslinking of cinnamic acid derivatives 1 and 2 with crosslinking agent 7 to produce the diester compound 8. Subsequent partial or complete acylation of diester 8 with an acylating agent, such as RC(O)L, affords acylated diester derivative 17.

Figure 2:
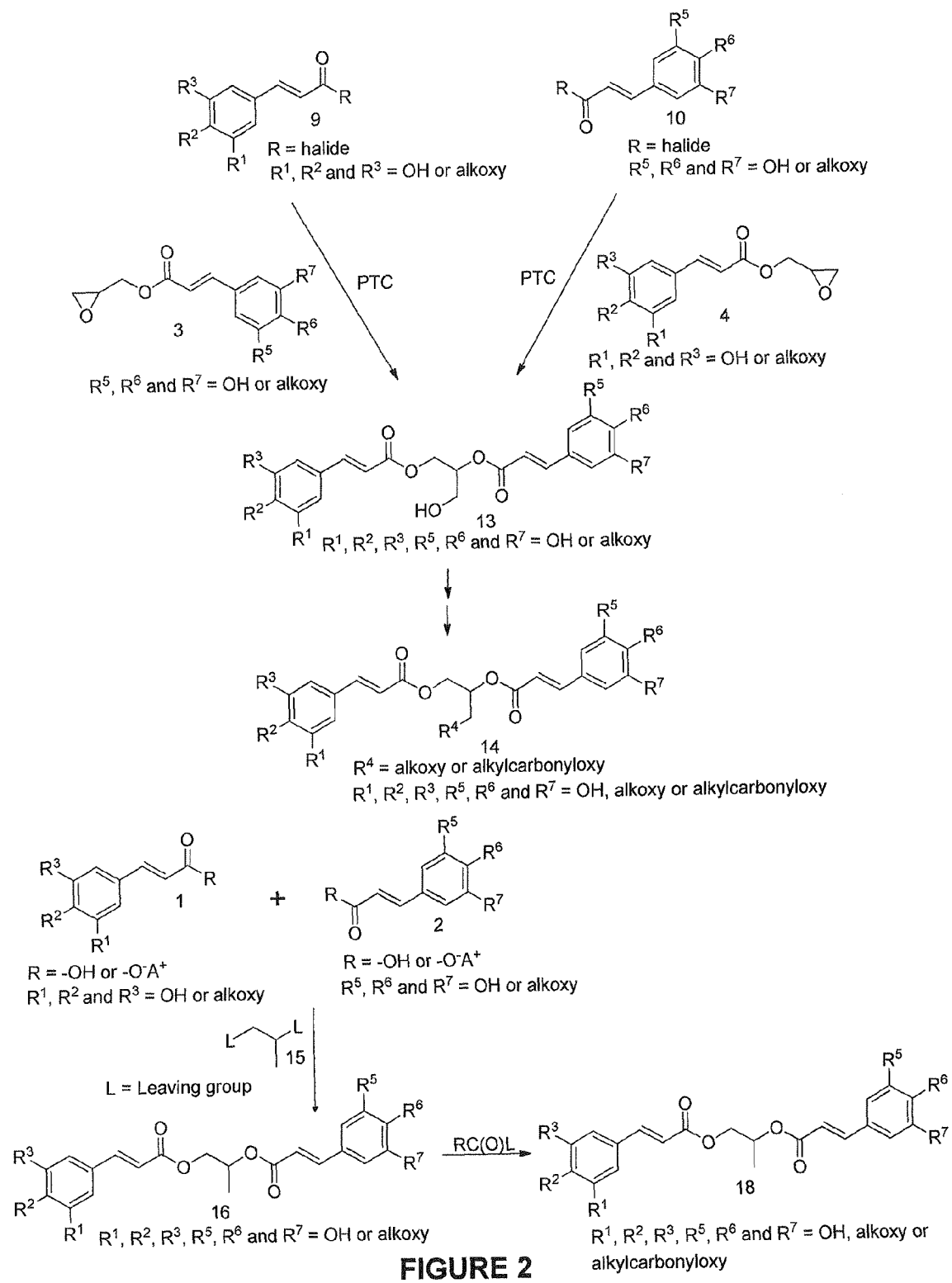
FIG. 2 illustrates examples of synthetic schemes for producing diester compounds of formula (II').

As illustrated in FIG. 2, compounds of formula (II') can be produced by esterification of cinnamic acid derivative 9 or 10 with the corresponding glycidyl cinnamate derivative 3 or 4 in the presence of a phase transfer catalyst (PTC) to afford 1,2 glycerol diester derivative 13, which can be further alkylated or acylated to produce diester 14.

Compounds of formula (II'), where $R^4$ is hydrogen, can be formed by crosslinking of cinnamic acid derivatives 1 and 2 with crosslinking agent 15 to produce the diester compound 16. Subsequent partial or complete acylation of diester 8 with an acylating agent, such as RC(O)L, affords acylated diester derivative 18.

Examples of phase transfer catalysts that can be used in forming the diester compounds 5 and 13 include tetrabutylammonium bromide or tetrabutylammonium chloride. The illustrated reactions for forming diesters 5, 6, 8, 13, 14 and 16-18 are conducted in a suitable inert solvent, such as dioxane, and carried out at a reaction temperature of 60-120° C. or 100-105° C.

Examples of the leaving groups that can be used in compounds 7 and 15 include, without limitation, a halogen, such as Cl, Br or iodo, methanesulfonyl, phenylsulfonyloxy, p-tosyloxy, methanesulfonyloxy, acetoxy or benzoyloxy.

Figure 3:
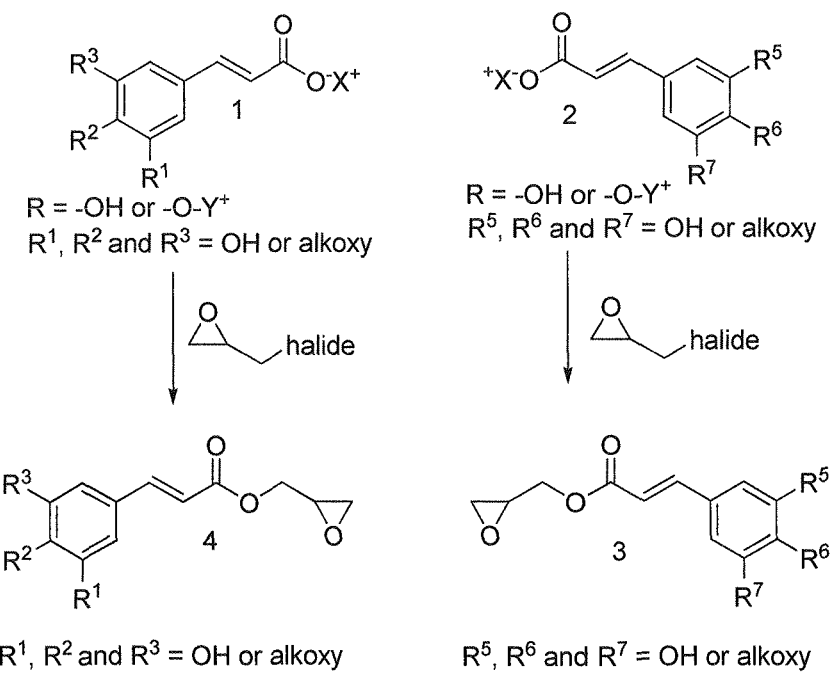
FIG. 3 illustrates examples of methods of producing glycidyl cinnamate derivatives.

Intermediate glycidyl cinnamate compounds 3 and 4 can be produced by a substitution reaction involving the corresponding cinnamate derivatives 1 or 2 and an excess molar amount of epichlorohydrin or other suitable epihalohydrin (FIG. 3). The reaction is conducted in a suitable inert solvent, such as dioxane, and optionally in the presence of a catalyst at a reaction temperature of about 50-100° C. or 70-95° C., for approximately 12 to 18 hours.

Figure 4:
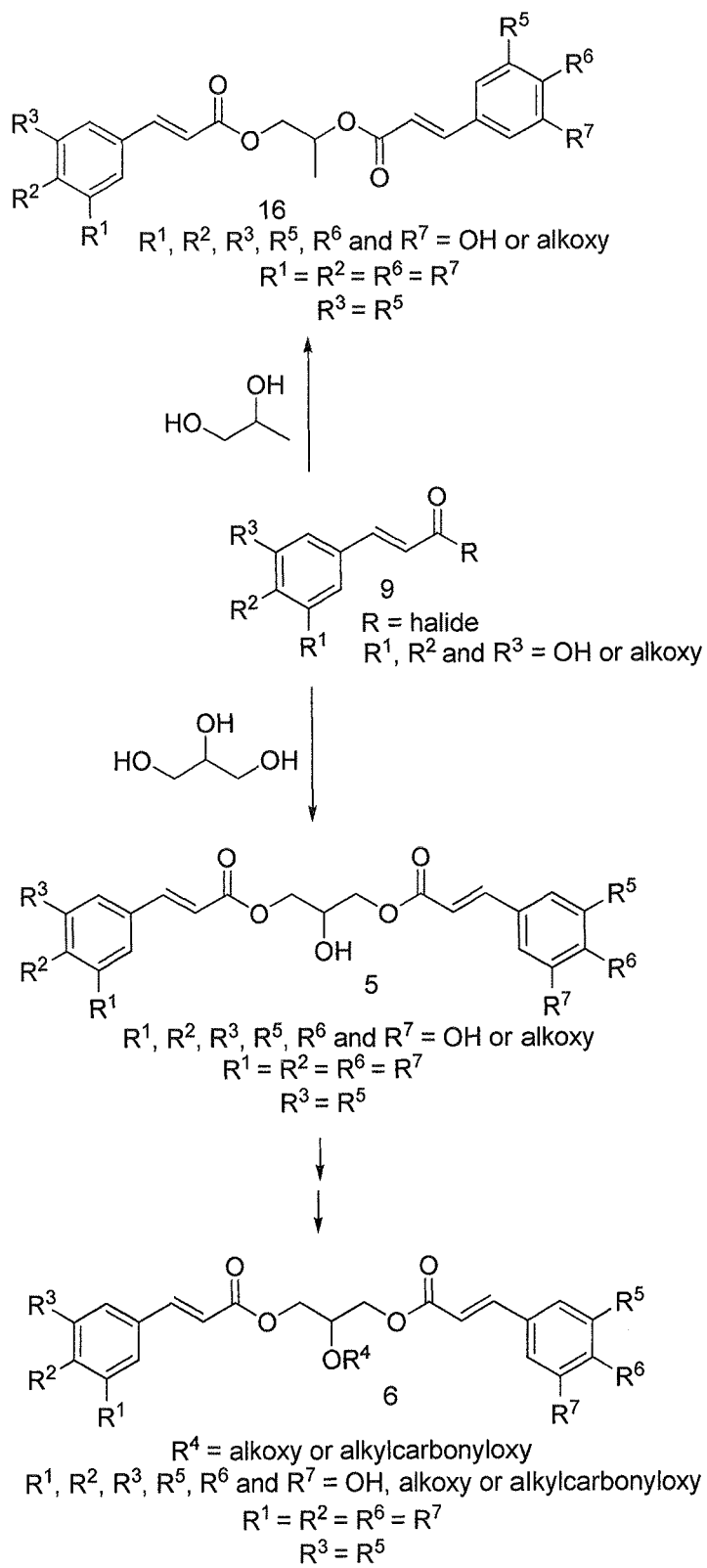
FIG. 4 illustrates examples of synthetic schemes for producing diester compounds of formulas (II) and (II') having symmetrical ends.

When the substituents $R^1$, $R^2$ and $R^3$ are the same as the substituents $R^7$, $R^6$ and $R^5$, respectively, compounds of the general formula (II) can be prepared in a reaction involving a cinnamyl halide derivative 9 and stoichiometric amounts of glycerol in the presence of a tertiary amine, such as pyridine, to produce the symmetrical 1,3 glycerol diester 5, which can be further alkylated or esterified to afford the protected compound 6 (FIG. 4).

To prepare compounds of general formula (II'), where the variable $R^4$ is H, and the variables $R^1$, $R^2$ and $R^3$ are equivalent to $R^7$, $R^6$ and $R^5$, respectively, the cinnamyl halide derivative 9 can be reacted with methylglycol in the presence of a catalytic amount of pyridine to produce the diester compound 16.

The cinnamyl halide derivative 9 or 10 can be prepared by reacting the corresponding derivative of cinnamic acid with a thionyl halide, such as thionyl chloride, in a suitable solvent, such as dioxane, at room temperature for approximately 15-20 minutes.

The reactions for forming diester derivatives 5, 8, 13 and 16 are typically carried out in the presence of pyridine and allowed to react for approximately 20-30 minutes. Following the completion of the reactions, the reaction mixture is neutralized with sodium bicarbonate or other suitable neutralizing agent. The reaction mixture is then filtered and the final compound is isolated by drying the organic layer under reduced pressure followed by crystallization from ethyl acetate or a mixture of ethyl acetate and cyclohexane.

Figure 5:
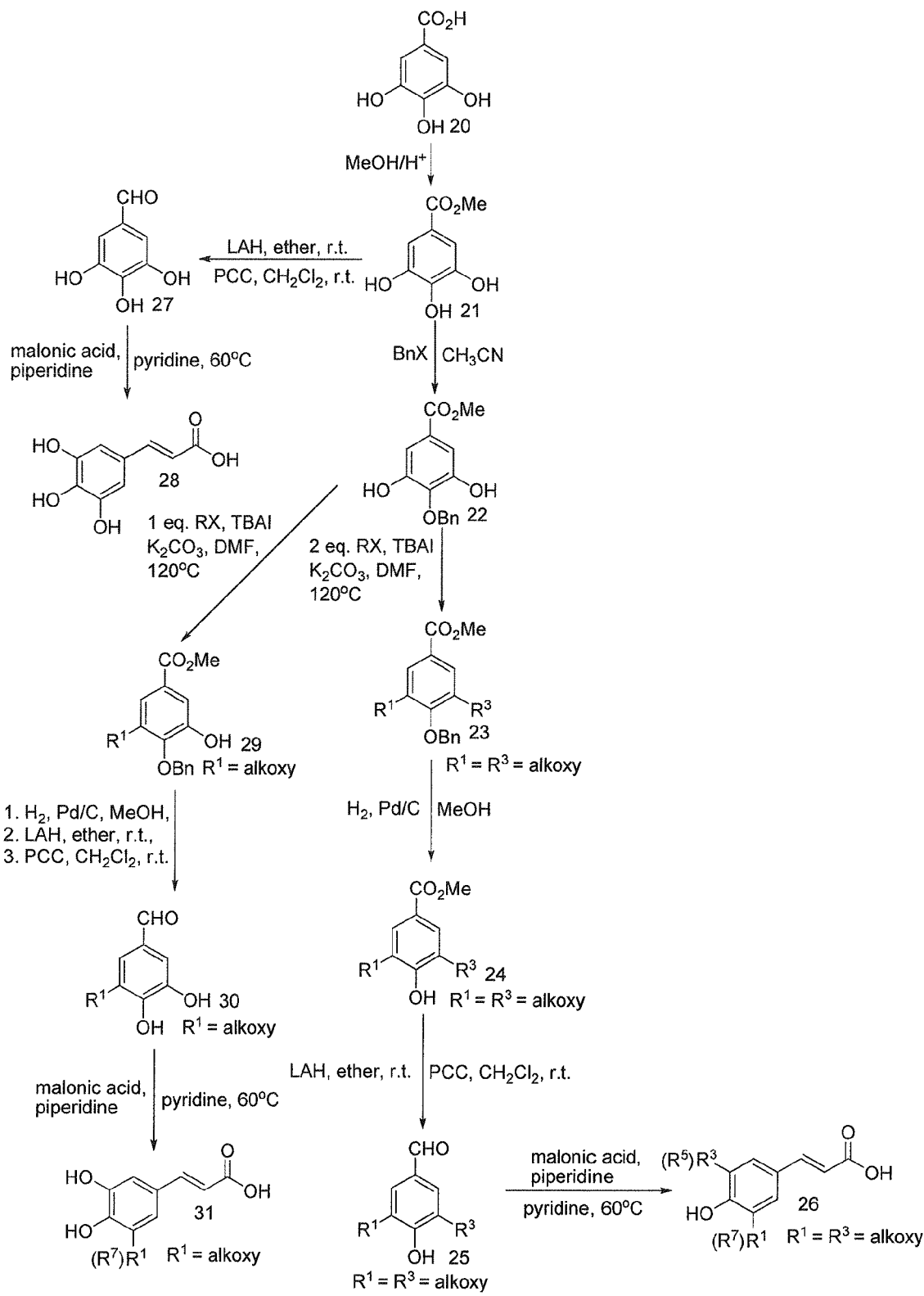
FIGS. 5 and 6 illustrate examples of synthetic schemes of forming tri-substituted derivatives of intermediates for forming the compounds of the present invention.
Figure 6:
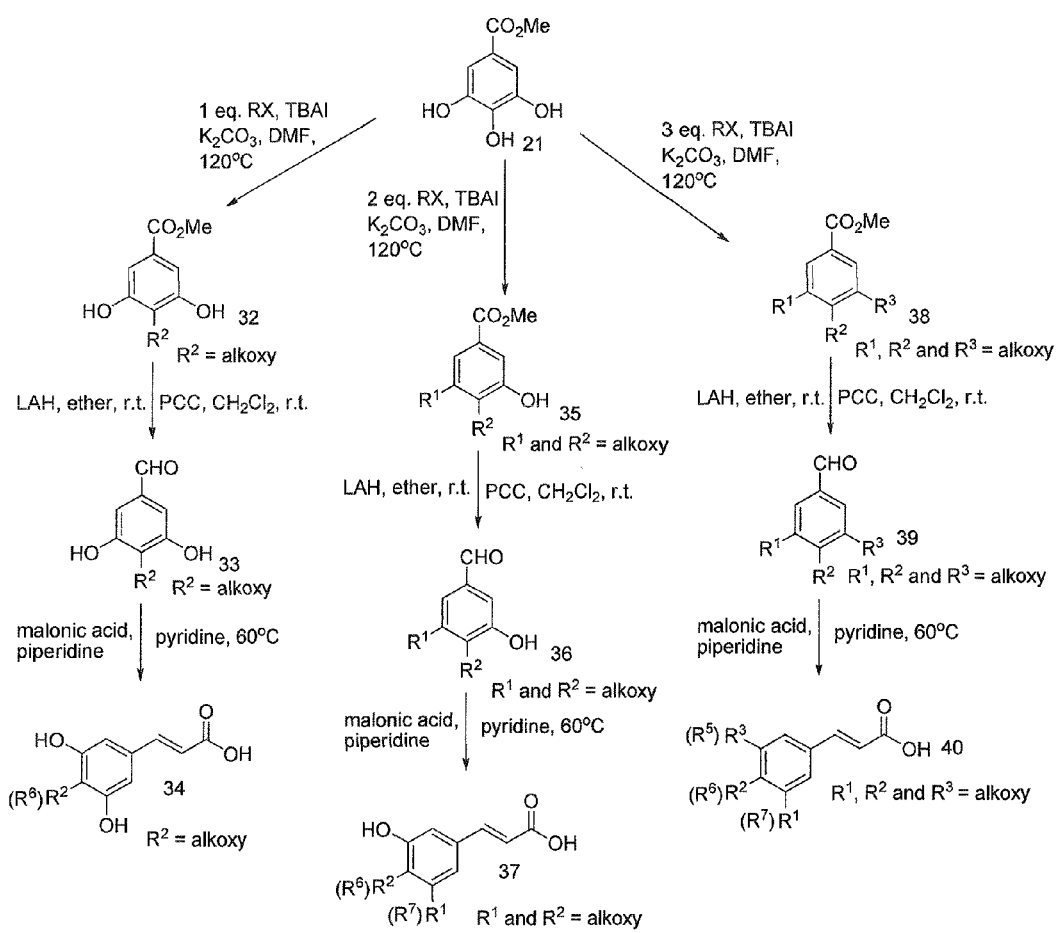

FIGS. 5 and 6 illustrate examples of synthetic schemes for producing different tri-substituted derivatives of cinnamic acids 1 and 2. Each of these schemes initially involves the esterification of gallic acid 20 to produce methyl gallate 21, which is selectively benzylated at the para position to produce protected derivative 22. Alkylation of derivative 22 with two equivalents of an alkyl halide RX affords dialkylated ester 23, which is subsequently subjected to hydrogenolysis to produce phenolic derivative 24. Reduction of phenol 24 with lithium aluminum hydride (LAH) following by partial oxidation of the resulting alkyl alcohol with pyridinium chlorochromate (PCC) results in the formation of aldehyde 25, which is allowed to react with malonic acid and piperidine in pyridine to produce cinnamic acid derivative 26.

Alternatively, methyl gallate 21 can be directly reduced and the resulting methylene alcohol partially oxidized with PCC to afford the aldehyde 27, which is subsequently allowed to react with malonic acid and piperidine in pyridine to produce cinnamic acid derivative 26.

In another example, alkylation of derivative 22 with one equivalent of an alkyl halide RX affords monolkylated ester 29, which is subsequently subjected to hydrogenolysis to remove the benzyl protecting group. The resulting phenol is then reduced with LAH to produce an methylene alcohol that is partially oxidized with PCC to form aldehyde 30, which is allowed to react with malonic acid and piperidine in pyridine to produce cinnamic acid derivative 31.

FIG. 6 illustrates examples of synthetic schemes for producing mono, di- and trialkylated derivatives of trihydroxylated cinnamic acid (34, 37 and 40). The synthetic schemes involve the initial reaction of methyl gallate 21 with 1, 2 or 3 eq. of an alkyl halide RX in the presence of tetrabutylammonium iodide and $K_2CO_3$ to produce the mono-alkylated ester 32, the di-alkylated ester 35 and the tri-alkylated ester 38, respectively. These esters are then subsequently reduced with LAH to produce respective alcohols that are partially oxidized with PCC to form aldehydes 33, 36 and 39, respectively, which are subsequently allowed to react with malonic acid and piperidine in pyridine to produce the alkylated cinnamic acid derivatives 34, 37 and 40, respectively.

Figure 7:
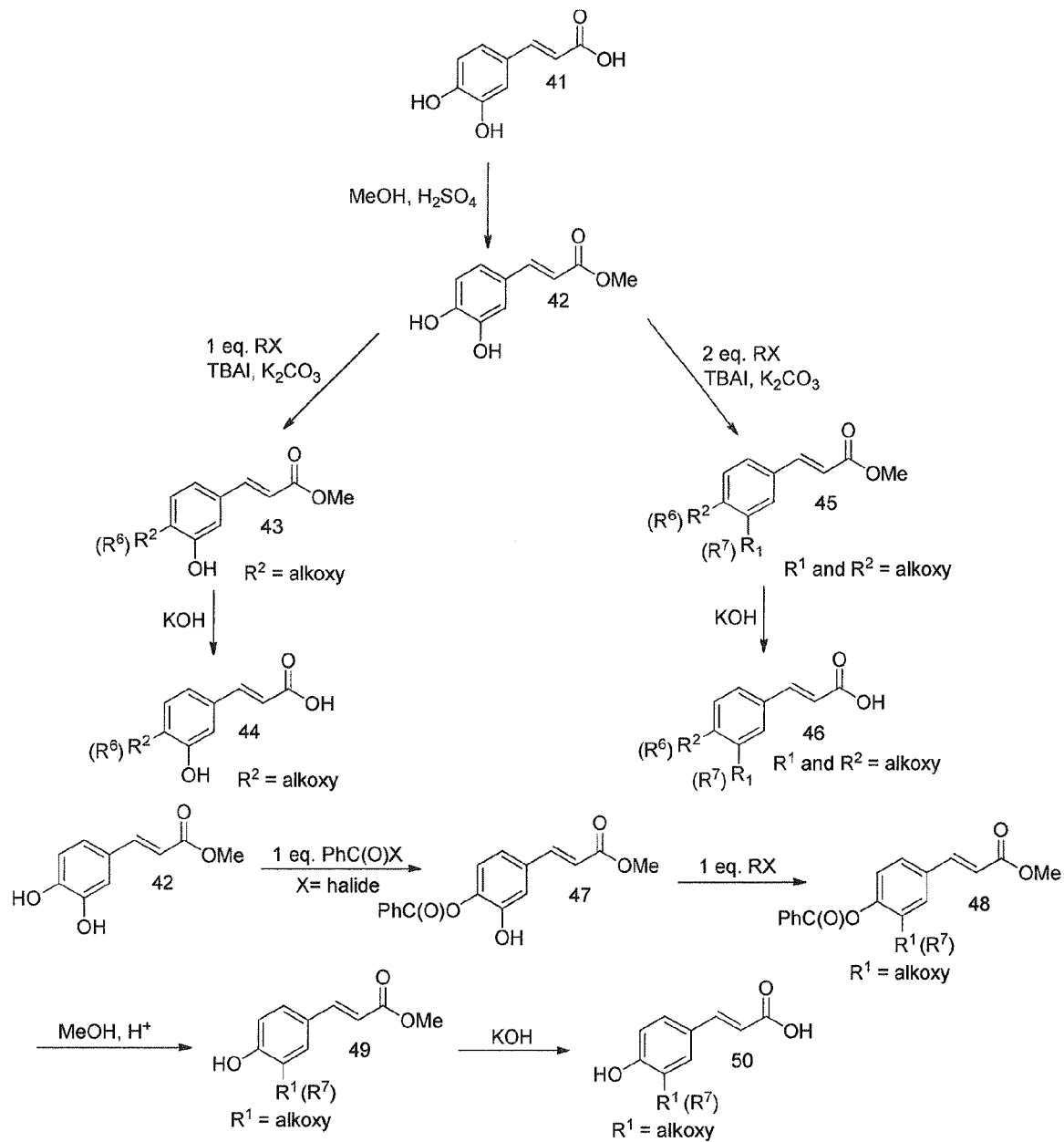
FIGS. 7 and 8 illustrate examples of synthetic schemes of forming di-substituted derivatives of intermediates for forming the compounds of the present invention.

FIG. 7 illustrates examples of synthetic schemes for producing mono and dialkylated derivatives of dihydroxylated cinnamic acid (44, 46 and 50). Caffeic acid 41 is first esterified in MeOH to produce caffeic acid methyl ester 42, which is then reacted with 1 or 2 eq. of an alkylating agent RX in the presence of TBAI and $K_2CO_3$ to produce the mono-alkylated intermediate 43 or the dialkylated intermediate 45. The esters 43 and 45 are then hydrolyzed under basic conditions to produce the corresponding acids 44 and 46, respectively.

To produce a derivative of caffeic acid having an alkoxy group in the 3-position of the benzene ring, the ester 42 is first protected with 1 eq. of a benzoyl halide to afford protected derivative 47 having a benzoyloxy group at the para-position of the phenyl ring, which is subsequently reacted with 1 eq. of an alkyl halide to produce mono-alkylated derivative 48. Deprotection of derivative 48 results in the production of ester 49 having an a free hydroxyl group at the para-position of the phenyl ring and an alkoxy group at the 3-position of the phenyl ring. Finally, hydrolysis of the ester 49 under basic conditions produces carboxylic acid 50.

Figure 8:
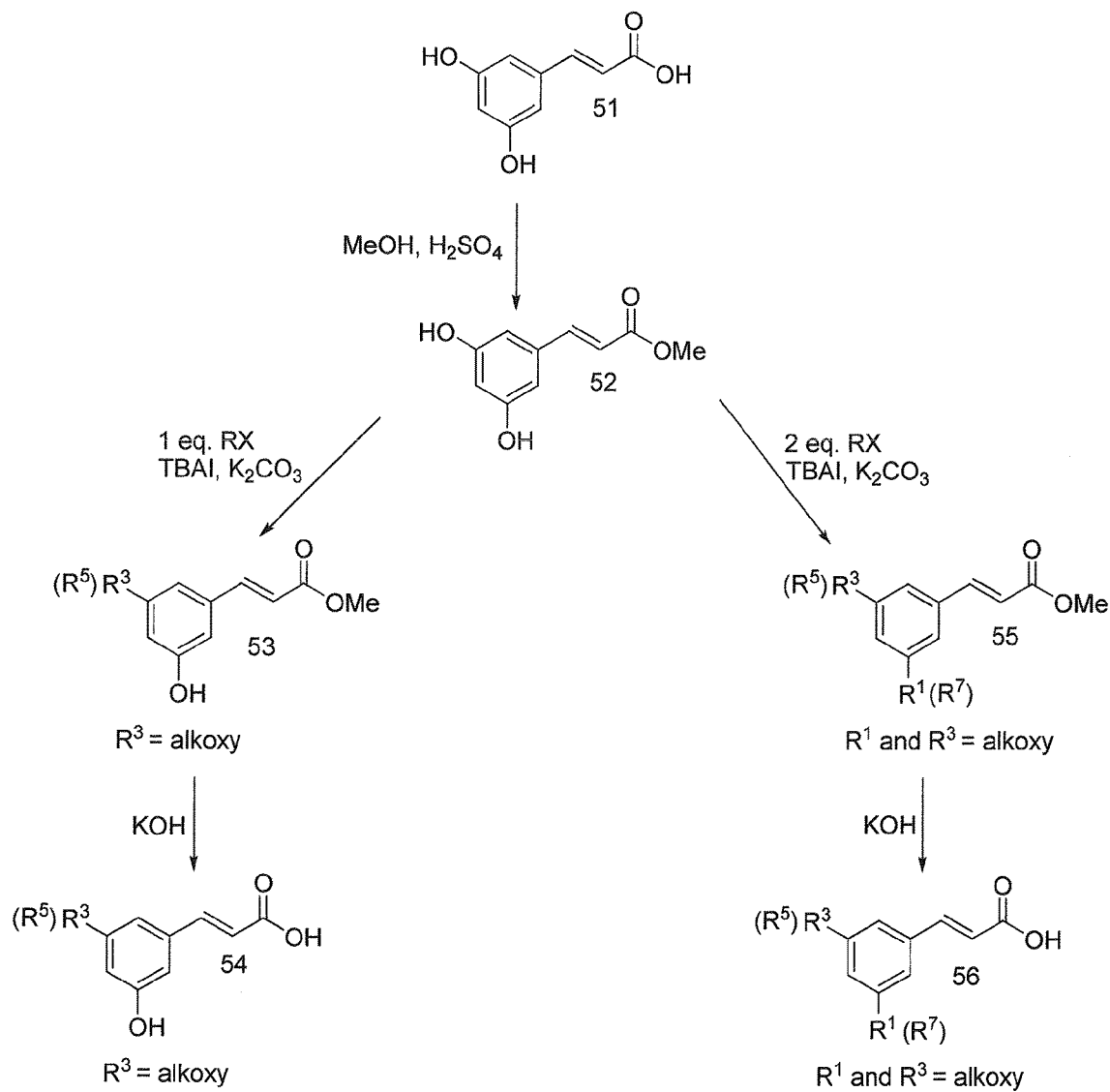

FIG. 8 illustrates examples of synthetic schemes for producing alkylated derivatives of 3,5-dihydroxycinnamic acid. In the illustrated synthetic schemes, 3,5-dihydroxycinnamic acid 51 is first esterified in MeOH to produce 3,5-dihydroxycinnamic acid methyl ester 52, which is then reacted with 1 or 2 eq. of an alkylating agent RX in the presence of TBAI and $K_2CO_3$ to produce the mono-alkylated intermediate 53 or the dialkylated intermediate 55. The esters 53 and 55 are then hydrolyzed under basic conditions to produce the corresponding acids 54 and 56, respectively.

Similarly, the monolkylated derivative of m- or p-coumaric acid can be produced by esterifying coumaric acid in MeOH to produce coumaric acid methyl ester, which is then reacted with an alkylating agent to produce a mono-alkylated intermediate. This intermediate is subsequently hydrolyzed under basic conditions to produce the corresponding alkylated derivative of m- or p-coumaric acid.

Figure 9:
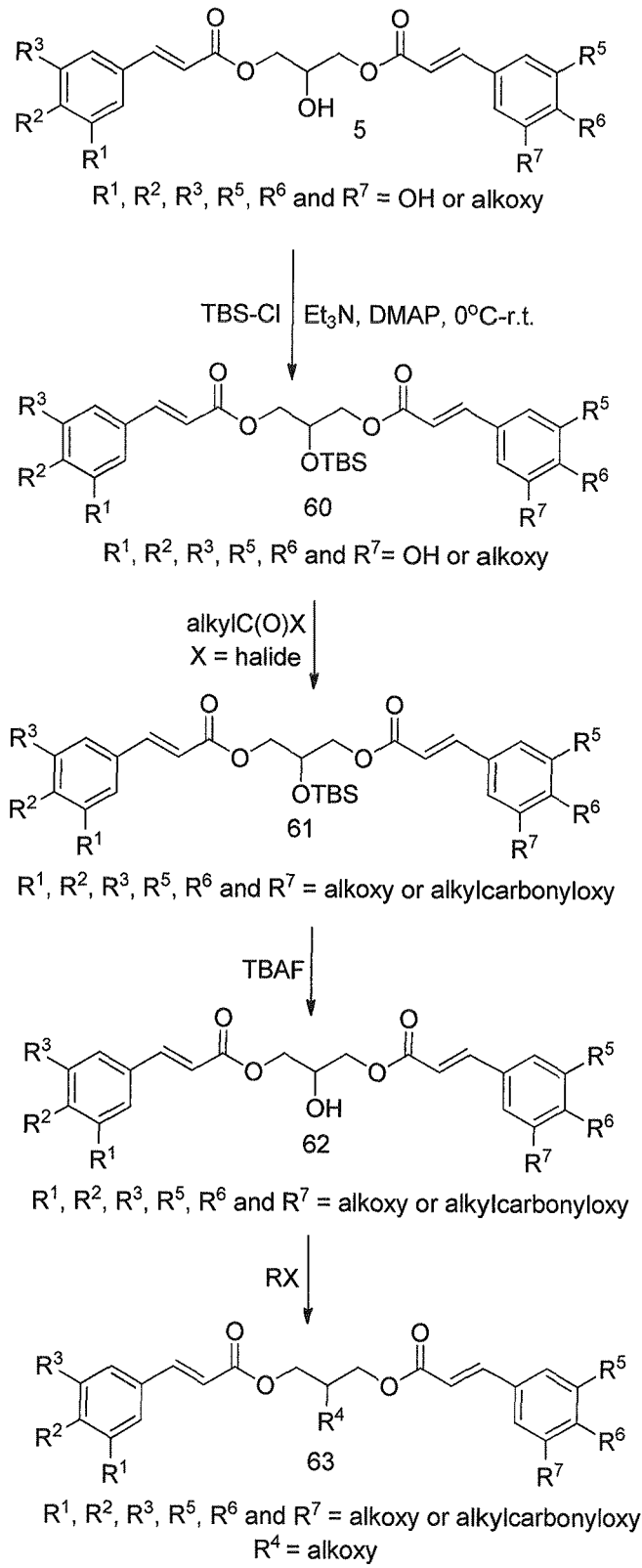
Figure 10:
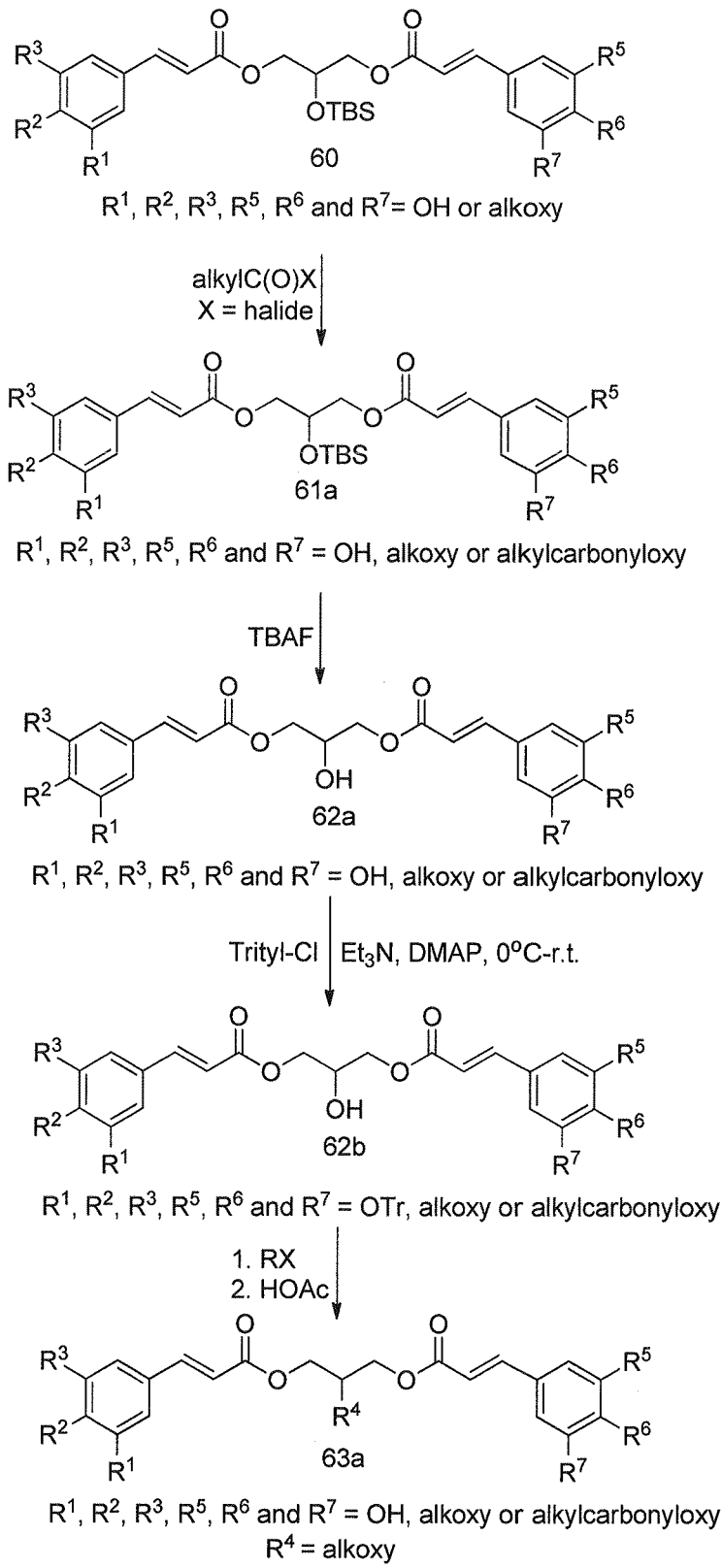
Figure 11:
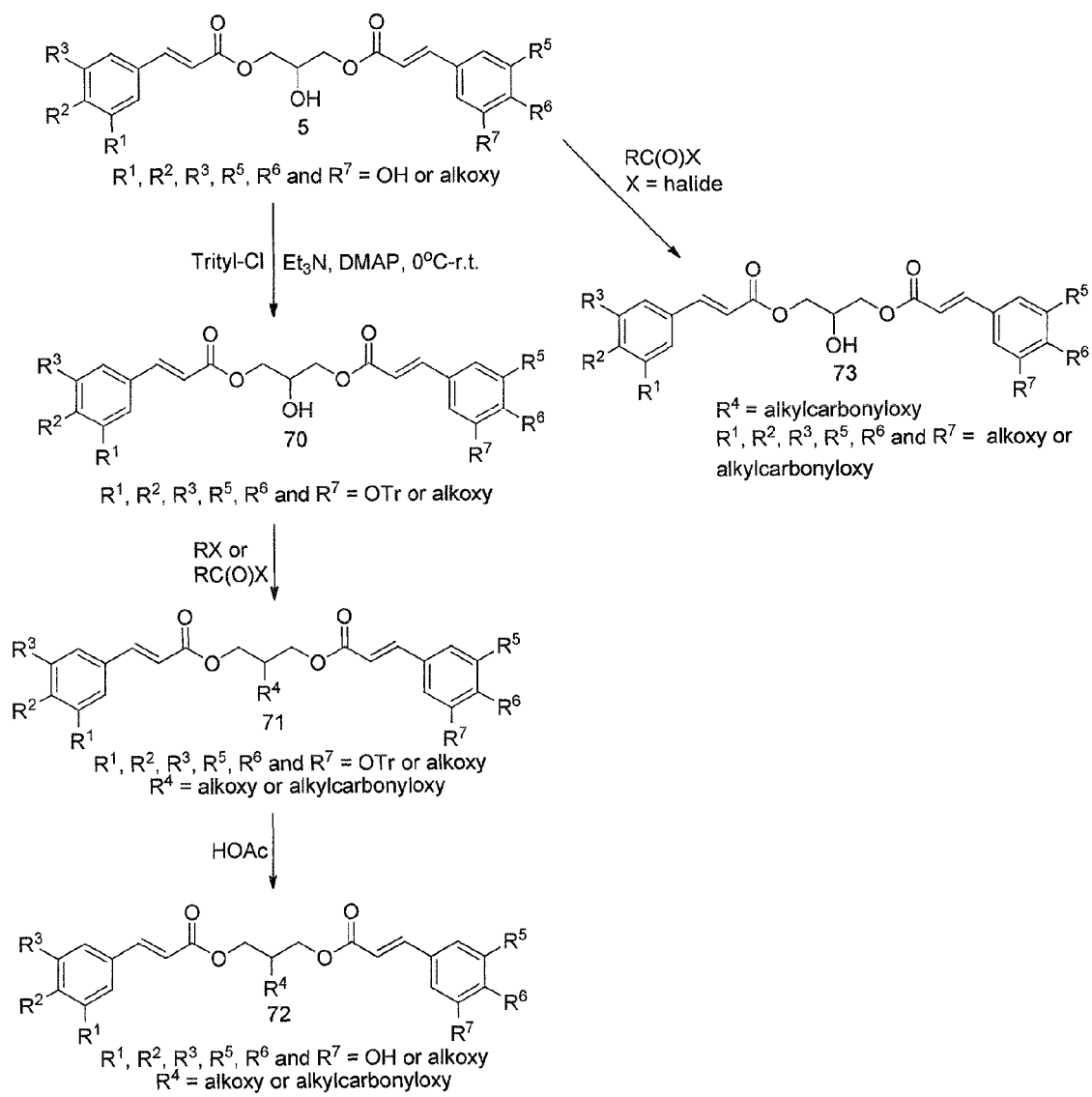
Figure 12:
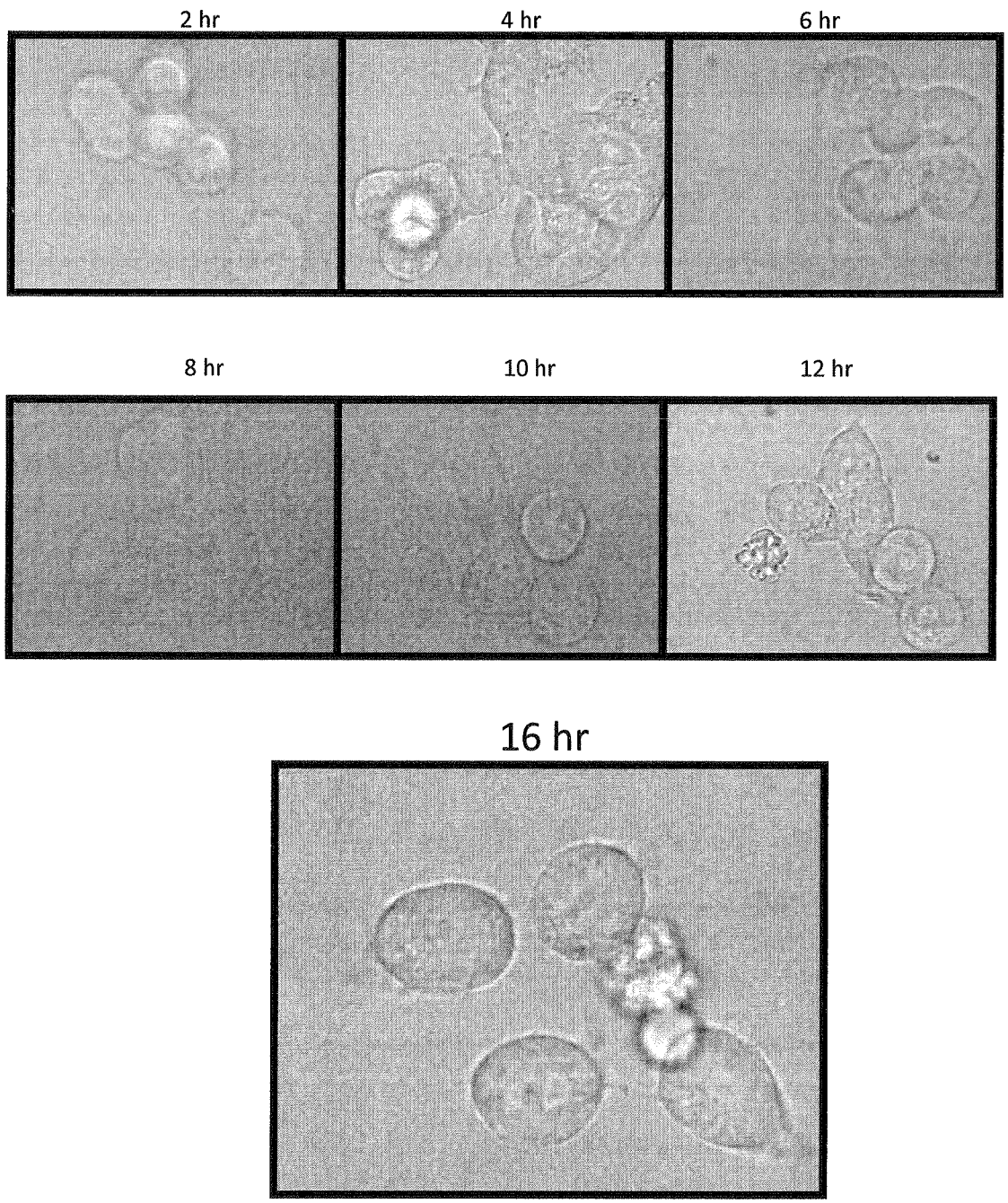
FIG. 12 shows micrographs of Human Colon Carcinoma HCT116 cells over time following treatment with no compound (control).
Figure 13:
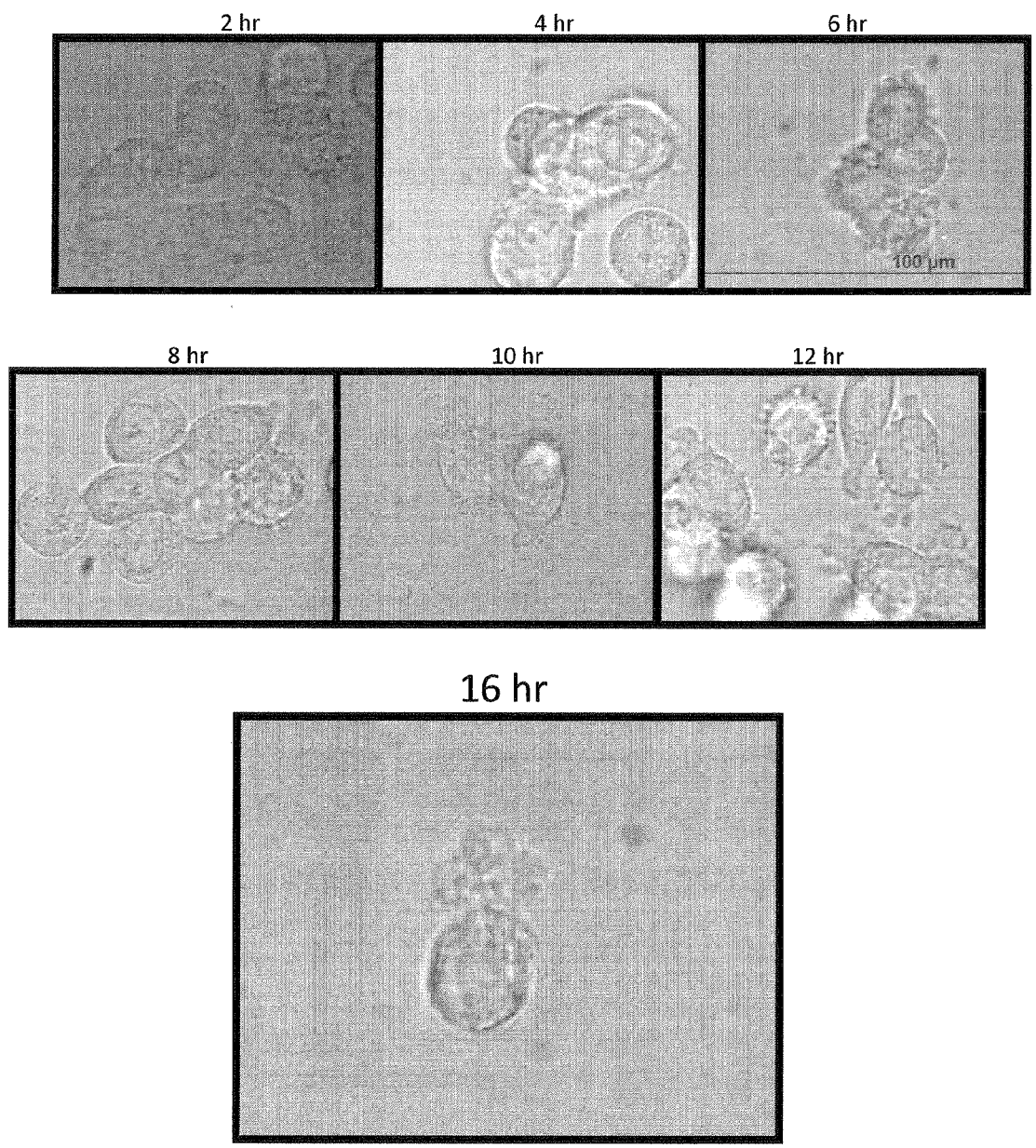
FIG. 13 shows micrographs of Human Colon Carcinoma HCT116 cells over time following treatment with 30 μM Compound (IIb).
Figure 14:
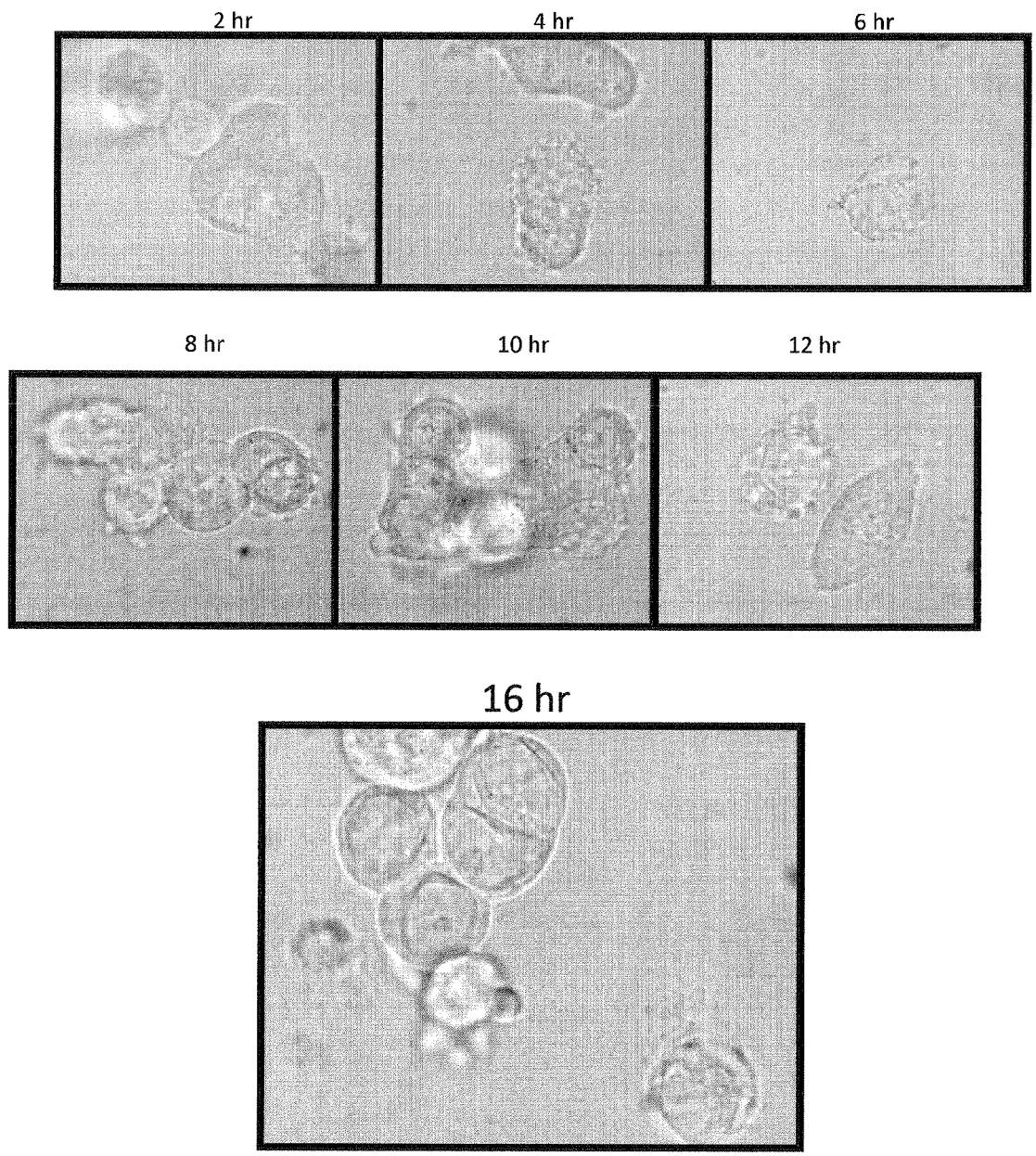
FIG. 14 shows micrographs of Human Colon Carcinoma HCT116 cells over time following treatment with 30 μM Compound (Ie)
Figure 15:
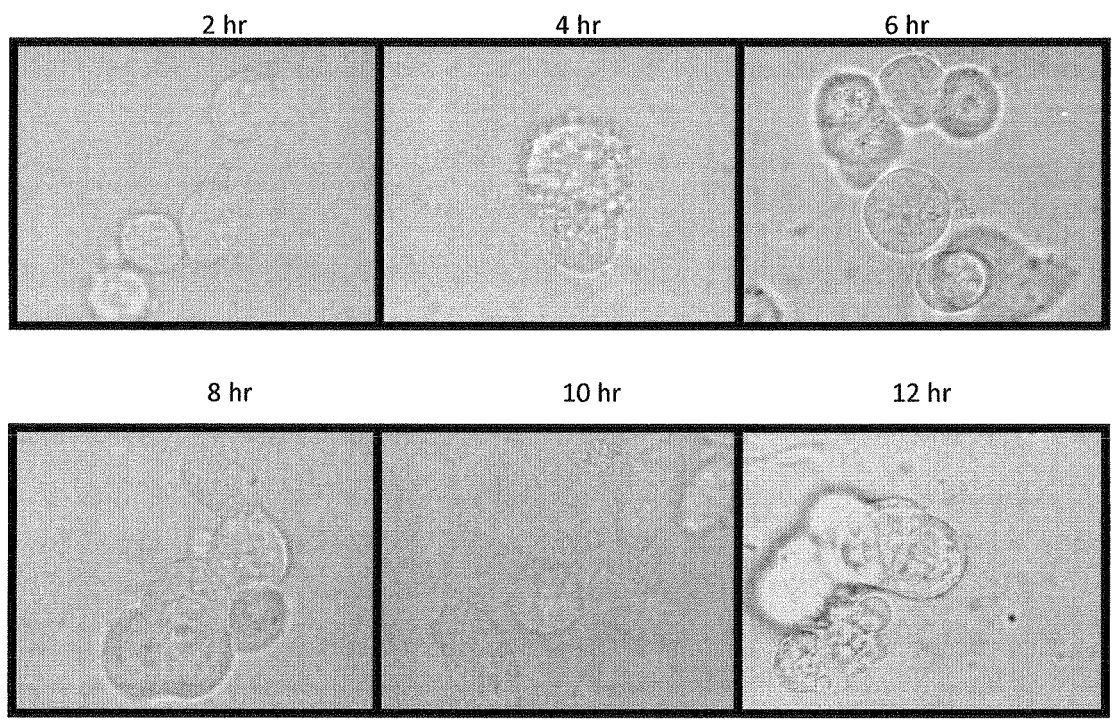
FIG. 15 shows micrographs of Human Colon Carcinoma HCT116 cells over time following treatment with 30 μM Compound (Id)

FIGS. 9-11 illustrate examples of synthetic schemes for forming different protected derivatives of the diesters 5 and 13. Referring to FIG. 9, there is shown an example of a synthetic scheme for forming diester derivatives having acylated phenolic residues, which involves first protecting the secondary hydroxyl group of diester 5 with a tert-butyldimethylsilyl (TBS) group to form the TBS-ether 60 and then acylating the free phenolic hydroxyl groups with an acylating agent, such as an acyl halide, to form the acylated, protected derivative 61. The TBS group is then removed with tetrabutyl ammonium fluoride (TBAF) to produce the alcohol 62, which can then be further alkylated to afford the acylated, alkyl ether 63.

In another example illustrated in FIG. 10, the phenolic hydroxyl groups of TBS ether 60 are partially acylated to form the TBS ether 61a having one or more free phenolic hydroxyl groups. Following deprotection of the TBS ether 61a with TBAF, the phenolic hydroxyl groups of the resulting alcohol 62a are selectively protected with trityl-Cl to form the tritylated derivative 62b having a free secondary hydroxyl group. The alcohol 62b can then be further alkylated to afford the partially acylated alkyl ether 63a.

In further examples illustrated in FIG. 11, the free phenolic hydroxyl groups and the secondary alcohol group of diester 5 can be acylated using an excess of an acylating agent, such as an acyl halide. Alternatively, the phenolic hydroxyl groups of diester 5 may be selectively protected with trityl-Cl to form the tritylated derivative 70 having a free secondary hydroxyl group. Subsequent alkylation or acylation of the alcohol 70 followed by deprotection of the phenolic hydroxyl groups results in alkylated or acylated derivative 72.

The following non-limiting examples are given to illustrate the invention:

EXAMPLES

Example 1

Preparation of Glycidyl Cinnamate (130)

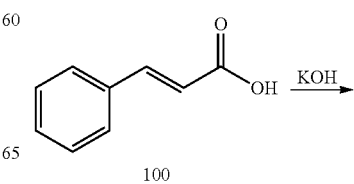

100

-continued

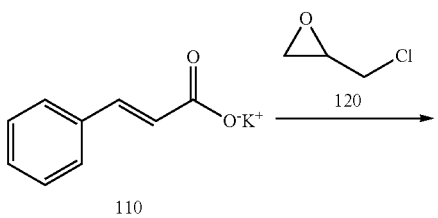

110

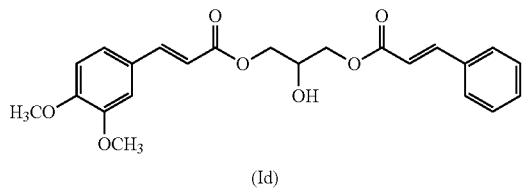

(Id)

3,4-dimethoxy cinnamic acid (140; 3.82 g; 18.37 mol) was dissolved in 60 mL of dioxane and heated under reflux (60°-70° C.). A catalytic amount (22.5 mg; 0.7 mmol) of tetrabutylammonium bromide and 1.5 g (7.35 mmol) of glycidyl cinnamate (130) were consecutively added to the solution of 3,4-dimethoxy cinnamic acid (140). The resulting mixture was heated to 100°-105° C. with continuous stirring for 15-16 h and then distilled under reduced pressure to yield compound (Id). $^1$H-NMR (CD$_3$OD) δ 3.81 (s, 3H), 3.83 (s, 3H), 4.14 (m, 1H), 4.27 (d, 4H, J=8 Hz), 6.42 (d, 1H, J=16 Hz), 7.64 (d, 1H, J=16 Hz), 7.15 (dd, 1H, J=8 Hz, 2 Hz), 6.92 (d, 1H, J=8 Hz), 7.18 (d, 1H, J=2 Hz), 6.53 (d, 1H, J=16 Hz), 7.70 (d, 1H, J=16 Hz), 7.35 (m, 3H), 7.56 (m, 2H)

130

To 5.66 g (0.10 mol) of potassium hydroxide dissolved in 50 mL of deionized water and heated to 50°-60° C. was added 15 g (0.10 mol) of cinnamic acid (100) with stirring. The resulting reaction slurry was dried in a vacuum oven at 40-50° C. to yield potassium cinnamate (110).

Alternative Method for Producing Potassium Cinnamate (110)

To a solution of cinnamic acid (100, 15 g, 0.10 mol) in THF (150 mL) at about 30° C. was added 5.66 g (0.10 mol) of a powder of freshly ground potassium hydroxide pellets to produce a white precipitate of potassium cinnamate (110). The precipitate was filtered and dried in a vacuum oven at 40-50° C.

Potassium cinnamate (110; 5.3 g; 0.028 mol) and a catalytic amount (0.85 g; 2.7 mmol) of tetrabutylammonium bromide were added to 50 g (0.54 mol) of epichlorohydrin (120) in a reaction vessel equipped with a mechanical stirrer and a reflux assembly and heated to 95°-105° C. to form a mixture that was allowed to react for 60 minutes. The mixture was then cooled to room temperature, diluted with 55 mL chloroform, and filtered to remove solid precipitates. The organic filtrate was washed sequentially with 50 mL of 5% NaHCO$_3$ and deionized water and the resulting organic layer was distilled under reduced pressure at 30°-40° C. to yield glycidyl cinnamate (130).

| Proton | Chemical Shift |
|---|---|
| 2, 6 | 7.56 |
| 3, 5 | 7.35 |
| 4 | 7.35 |
| 7 | 7.70 |
| 8 | 6.53 |
| 2' | 7.18 |
| 5' | 6.92 |
| 6' | 7.15 |
| 7' | 7.64 |
| 8' | 6.42 |
| 10, 10' | 4.27 |
| 11 | 4.14 |
| OCH3 | 3.83 |
| OCH3 | 3.81 |

Example 2

Preparation of (E)-3-(cinnamoyloxy)-2-hydroxypropyl 3-(3,4-dimethoxyphenyl)acrylate (Id)

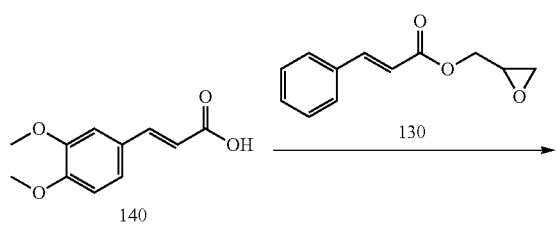

Example 3

Preparation of (E)-oxiran-2-ylmethyl 3-(3,4-dimethoxyphenyl) (170)

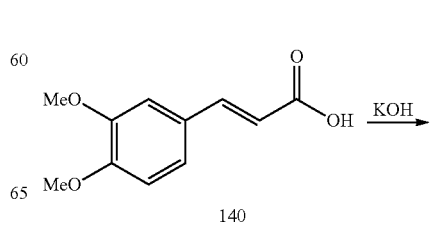

21

-continued

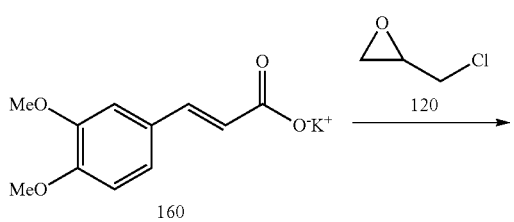

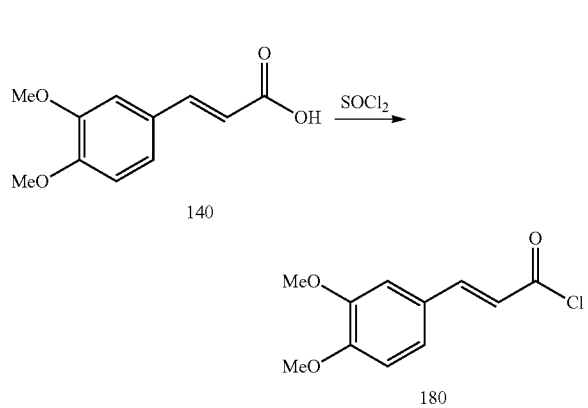

To 5.0 g (0.24 mol) of potassium hydroxide dissolved in 30 mL of deionized water and heated to 50°-60° C. was added 1.34 g (0.024 mol) of 3,4-dimethoxy cinnamic acid (140) with stirring. The resulting reaction slurry was dried in a vacuum oven at 40-50° C. to yield potassium 3,4-dimethoxy cinnamate (160).

Potassium 3,4-dimethoxy cinnamate (160; 11.83 g; 0.048 mol) and 0.772 g (0.0024 mol) of tetrabutylammonium bromide were added to 55.32 g (0.60 mol) of epichlorohydrin (120) in a reaction vessel equipped with a mechanical stirrer and a reflux assembly to form a mixture that was allowed to react for 60 minutes and heated at 80°-90° C. The mixture was then cooled to room temperature, filtered to remove solid precipitate and dried under vacuum to yield Compound 170.

Example 4

Preparation of (E)-3-(3,4-dimethoxyphenyl)acryloyl chloride (180)

To 5 mL of dried thionyl chloride (SOCl₂) contained in a reaction vessel was slowly added 4 g (19 mmol) of 3,4-dimethoxy cinnamic acid (140) and 50 µl of dried N′N′-dimethylformamide. The contents of the reaction vessel were mixed continuously at room temperature for 10-15 minutes, and the resulting product was dried in vacuo at 30-40° C. to yield (E)-3-(3,4-dimethoxyphenyl)acryloyl chloride (180).

22

Example 5

Preparation of (E)-2-(cinnamoyloxy)-3-hydroxypropyl 3-(3,4-dimethoxyphenyl)acrylate (Id′)

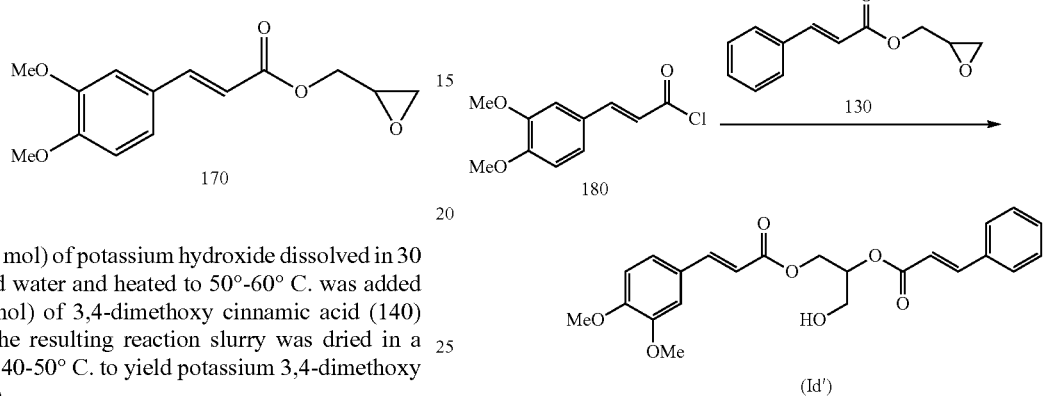

To 3,4-dimethoxy cinnamoyl chloride (180; 2.5 g; 11 mmol) dissolved in 20 mL of dioxane was added a catalytic amount (250 mg) of tetrabutylammonium bromide and 1.33 g (6.5 mmol) of glycidyl cinnamate (130). The resulting mixture was heated under reflux (90°-95° C.). with continuous stirring for 16-17 h and then distilled under reduced pressure to yield compound (Id′).

Example 6

Preparation of Caffeoyl Chloride (200)

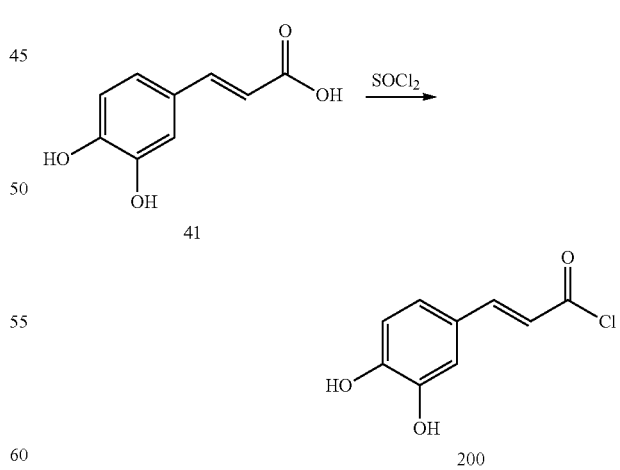

500 mg (2.78 mmol) of caffeic acid (190) was dissolved in 12 mL of dried dioxane at room temperature and then 600 µL of SOCl₂ (thionyl chloride) was slowly added with mixing over approximately 20 minutes to produce a reaction mixture containing caffeoyl chloride (200).

Example 7

Preparation of (2E,2'E)-2-hydroxypropane-1,3-diyl bis(3-(3,4-dihroxyphenyl)acrylate (IIb)

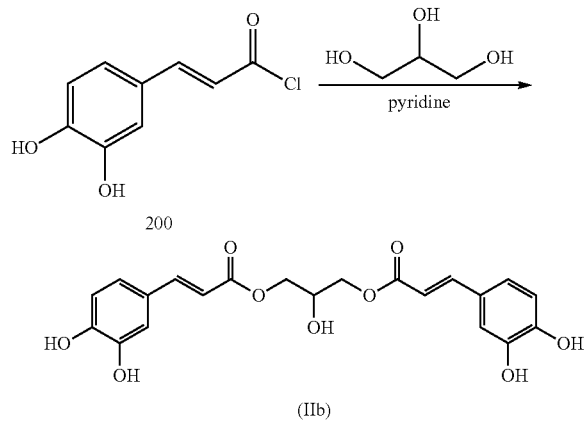

To the crude reaction mixture of Example 6 was added 248 mg (1.39 mmol) of anhydrous glycerol and a catalytic amount (300 μL) of pyridine. The mixture was stirred for 30-40 minutes, and then approximately 1.0 g of NaHCO$_3$ and 10 mL of a methanol-ethyl acetate (50:50) mixture was added. After about 30 minutes of further stirring at room temperature, the reaction mixture was filtered and the solvent was removed. The reaction mixture was then dried under reduced pressure at approximately 60° C. The dried material was dissolved in 50 mL ethyl acetate, and washed three times with 100 mL ammonium formate, pH 3.7. The washed organic layer was dried over Na$_2$SO$_4$ and then under reduced pressure to obtain compound (IIb). Compound (IIb) was then recrystallized from a mixture of ethyl acetate and cyclohexane (1:3). $^1$H-NMR (CD$_3$OD) δ 4.15 (m, 1H), 4.27 (m, 4H), 6.32 (d, 2H, d=16 Hz), 7.60 (d, 2H, J=16 Hz), 6.95 (dd, 2H, J=8, 2 Hz), 6.77 (d, 2H, d=8 Hz), 7.05 (d, 2H, J=2 Hz)

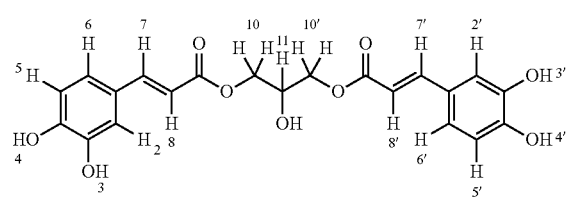

| Proton | Chemical Shift |
|---|---|
| 2, 2' | 7.05 |
| 5, 5' | 6.77 |

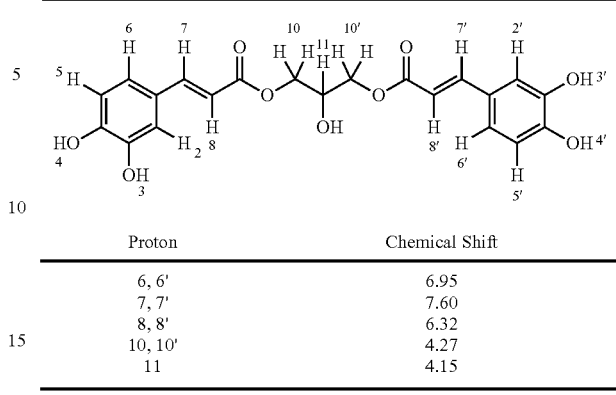

| Proton | Chemical Shift |
|---|---|
| 6, 6' | 6.95 |
| 7, 7' | 7.60 |
| 8, 8' | 6.32 |
| 10, 10' | 4.27 |
| 11 | 4.15 |

Example 8

Preparation of potassium 3-(4-hydroxyphenyl)acrylate (200)

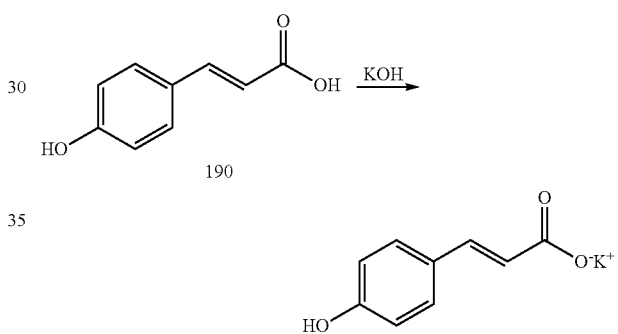

To 15 mL of a 0.002 mM aqueous solution of potassium hydroxide was slowly added 5 g coumaric acid 190 (30 mmol) with mixing at 60-70° C. The resulting potassium coumarate (200) was dried under vacuum at 30-40° C.

Example 9

Preparation of (E)-3-((E)-3-(3,4-dimethoxyphenyl)acryloyoxy)-2-hydroxypropyl 3-(4-hydroxyphenyl)acrylate (IIc)

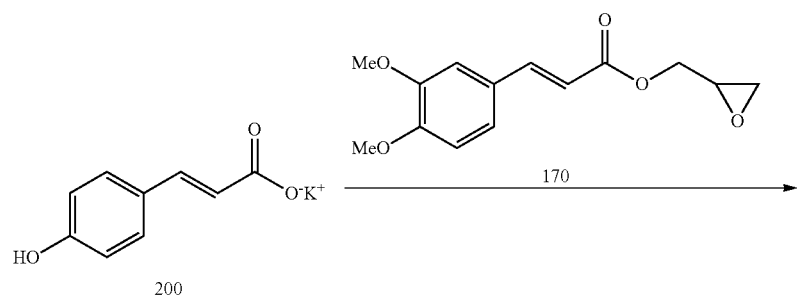

-continued

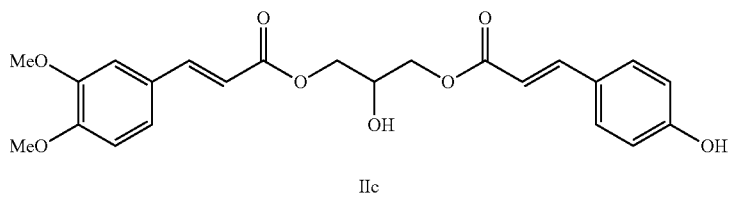

IIc

To a solution of 1.5 g (5.68 mmol) of oxiran-2-ylmethyl 3-(3,4-dimethoxyphenyl)acrylate (170) dissolved in 30 mL of dried dioxane was added 2.29 g (11.36 mmol) of potassium coumarate (200) dissolved in 20 mL dioxane and 100 mg of tetrabutylammonium bromide, and the resulting mixture was heated to a temperature of 105-110° C. for 16-18 hours to produce diester (IIc).

Example 10

Preparation of (E)-3-(cinnamoyloxy)-2-hydroxypropyl 3-(3,4-dihydroxyphenyl)acrylate (Ie)

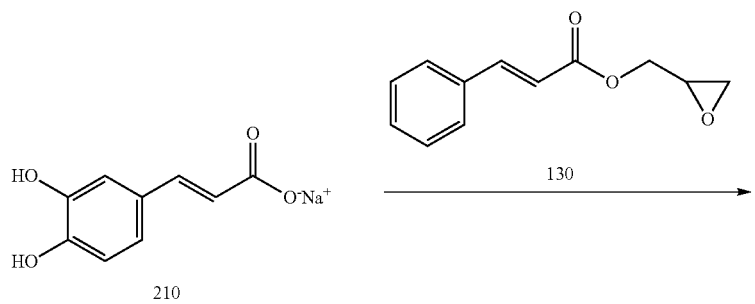

(Ie)

Caffeic acid (41; 18.02 g; 0.10 mol) was dissolved in THF (180 mL) with stirring at about 30° C. to yield a 10% solution. A powder of freshly ground sodium hydroxide pellets (4.00 g; 0.10 mol) was added to the caffeic acid solution and a solid precipitate of sodium caffeate (210) was formed, which was filtered and dried under reduced pressure.

To a solution of sodium caffeate (210; 7.35 mmol) in DMSO (20 mL) at 60°-70° C. was added glycidyl cinnamate (130; 7.35 mmol). The resulting mixture was heated to 60°-75° C. with continuous stirring for 22-24 h and then distilled under reduced pressure to yield compound (Ie). $^1$H-NMR (CD$_3$OD) δ 4.16 (s, 1H), 2.28 (s, 4H), 6.29 (d, 1H, J=16 Hz), 6.65 (d, 1H, J=16 Hz), 6.75 (d, 1H, J=8 Hz), 6.93 (1H, dd, J=8, 2 Hz), 7.03 (d, 1H, J=2 Hz), 7.37 (m, 1H), 7.38 (m, 1H), 7.55 (m, 1H), 7.59 (d, 1H, J=16 Hz), 7.72 (d, 1H, J=16 Hz).

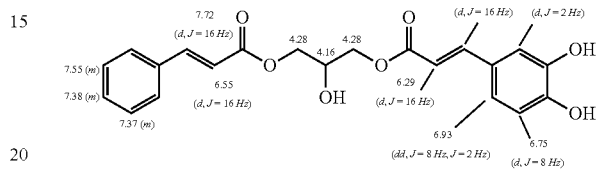

Anti-Cancer Activity

The compounds prepared in the present invention exhibited good in vitro anticancer activity towards human B-16 melanoma cell lines. The cell lines were maintained in EMEM medium supplemented with 10% FCS, 0.1% sodium bicarbonate and 12 mM glutamine. In a typical procedure, 1×10$^4$ cells were seeded into each of 96 well plate in 90 μL volume of medium. The plates were incubated for 24 h in the presence of CO$_2$ to allow for cell attachment. After 24 h, test compounds were evaluated at five 10 fold dilutions from 1:10, 1:100, 1:1000, 1:10000 and 1:100000. To each test well 100 μL of test compound solution was added and the medium with vehicle was added to control wells and the plates were further incubated. After 24 h of incubation, 10 μL of [3H]-thymidine was added to each well to obtain a 1 μCi concentration per well and incubated for a further 24 h. The plates were terminated, cells harvested and read by microbeta plate reader. The results are shown in Table 1.

TABLE 1

Values of EC$_{50}$ of compounds of the present invention in the B-16 melanoma cell line, µM

| Compound | EC$_{50}$ (µM) |
|---|---|
| 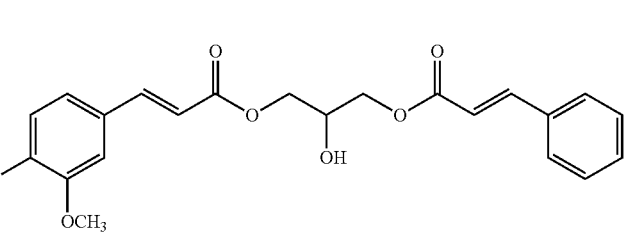 (Id) | 1.08 |
| 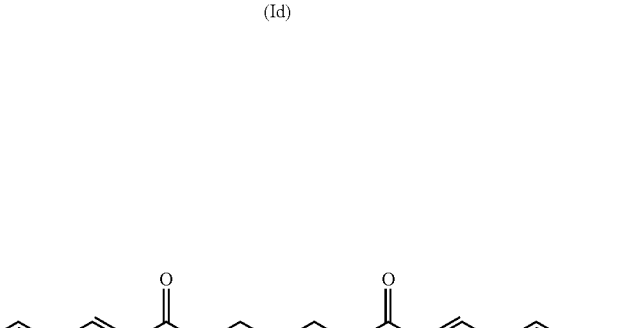 (IIb) | 6.12 |

MTT (Cell Proliferation and Viability) Assay for Anticancer Compounds of the Present Invention Normal human fibroblast cell lines (GM9503 and GM8399) and human carcinoma cell lines MCF-7, A549, HCT116, SKOV-3 and PC-3 were maintained in DMEM (Dulbeco's Modified Essential Medium) supplemented with 10% FBS (Fetal Bovine Serum). In addition, murine leukemia MDAY-D2 cells were maintained in RPMI 1640 media supplemented with 5% FBS. All media were supplemented with 100 units/mL of streptomycin and 100 µg/mL of penicillin (all from Hyclone, Logan, Utah). Cells were incubated in a humidified air atmosphere containing 5% CO$_2$ at 37° C.

Cell growth and viability were measured using the 3-(4,5-dimethythiazol-2-yl)-2,5-diphenyl tetrazolium bromide (MTT) reduction assay. MTT reagent (Sigma, St. Louis, Mo.) was prepared at 5 mg/ml in ddH$_2$O (5× solution), filter sterilized and stored in the dark at −20° C.

To determine the optimal number of cells to seed per well, preliminary experiments were conducted examining increasing cell densities in 96 well plates. Cell were seeded at various densities and examined under the microscope after 96 h. Based on these experiments and growth curve analyses, optimal cell densities were selected for each cell line. In brief, exponentially growing cells were harvested and 100 µL of cell suspension containing approximately 2000 cells was plated in 96-well microtiter plates. After 24 hours of incubation to allow for cell attachment, cells were treated with varying concentrations of test samples in medium (60 µL/well) supplemented with 5% FBS and incubated for 72 h at 37° C. under 5% CO$_2$. Three hours after the addition of MTT, the amount of formazan formed was measured spectrophotometrically at 570 nm with a Spectramax Plus 384 plate reader.

To assess the effects of the novel compounds on growth and viability, GM9503 (normal human fibroblast cells; 2.08×10$^3$ cells/well), GM8399 (normal human fibroblast cells; 2.04× 10$^3$ cells/well), A549 (human lung carcinoma cells; 2.05×10$^3$ cells/well), HCT116 (human colon carcinoma cells; 2.19× 10$^3$ cells/well), MCF-7 (human breast carcinoma cells; 2.19× 10$^3$ cells/well), SKOV-3 (human ovarian carcinoma cells; 2.10×10$^3$ cells/well), PC-3 (human prostate carcinoma cells; 2.08×10$^3$ cells/well) and MDAY-D2 (murine leukemia cells; 2.5×10$^3$ cells/well) were seeded in 96 well plates in supplemented medium. Twenty-four hours post-seeding, cells were treated with either DMEM supplemented with 5% FBS (as a control) or with compounds (IIb), (Ie) and (Id) at increasing concentrations. After incubation for 72 h, cell growth and viability were measured. Each compound was tested in triplicate and the data shown in Tables 2-4 represent the mean of viable cells compared to medium control.

TABLE 2

In-vitro inhibition of carcinoma cells, comparative EC$_{50}$ (μM)

| Compound | Human (EC$_{50}$) μM | | | | Murine (EC$_{50}$) μM MDAY-D2 (Leukemia) |
|---|---|---|---|---|---|
| | MCF-7 (Breast Carcinoma) | A549 (Lung Carcinoma) | HCT116 (Colon Carcinoma) | GM9503 (Normal Skin Fibroblast) | |
| (IIb) | 1.0 | 2.17 | NE* | 57.9 | 3.4 |
| (Ie) | 25.9 | 0.64 | 59.2 | NE* | 1.5 |
| (Id) | 72.2 | 0.59 | 102.5 | NE* | 5.0 |
| DMSO | NE* | NE* | NE* | 20.3 | 43.6 |

*NE (no significant inhibitory effect)

TABLE 3

In-vitro inhibition of carcinoma cells, comparative IC$_{50}$ (μM)

| Compound | Anticancer Compound Inhibition Concentration (IC$_{50}$) μM in human carcinoma cell lines | | | | |
|---|---|---|---|---|---|
| | A549 (Lung) | MCF-7 (Breast) | HCT116 (Colon) | PC-3 (Prostate) | SKOV-3 (Ovarian) |
| paclitaxel | 0.69 | 11.7 | 0.59 | 1.32 | 0.75 |
| (IIb) | 21.04 | 74.46 | 26.98 | 6.76 | 15.78 |

TABLE 3-continued

In-vitro inhibition of carcinoma cells, comparative IC$_{50}$ (μM)

| | Anticancer Compound Inhibition Concentration (IC$_{50}$) μM in human carcinoma cell lines | | | | |
|---|---|---|---|---|---|
| Compound | A549 (Lung) | MCF-7 (Breast) | HCT116 (Colon) | PC-3 (Prostate) | SKOV-3 (Ovarian) |
| 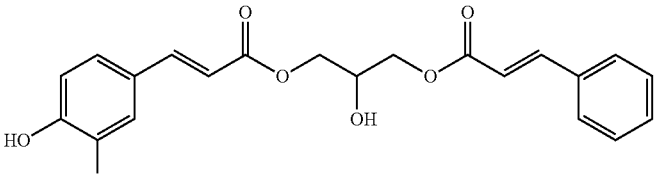 (Ie) | 33.2 | 33.02 | 27.88 | 9.04 | 16.52 |
| 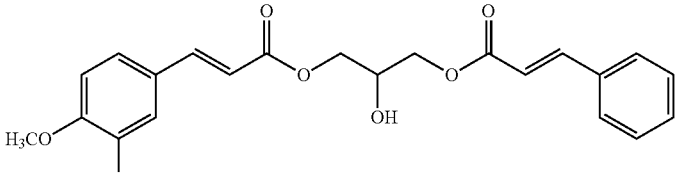 (Id) | 18.18 | 85.15 | 11.49 | 9.07 | 22.01 |

TABLE 4

Comparative Toxicity of compounds of the present invention in normal human fibroblast cells in-vitro (IC$_{50}$, μM)

| | Inhibition Concentration (IC$_{50}$) μM | |
|---|---|---|
| Compound | GM9503 (Normal human fibroblast) | GM8399 (normal human fibroblast) |
| paclitaxel | 0.7 | 2.1 |
| caffeic Acid | 22.0 | 24.0 |
| 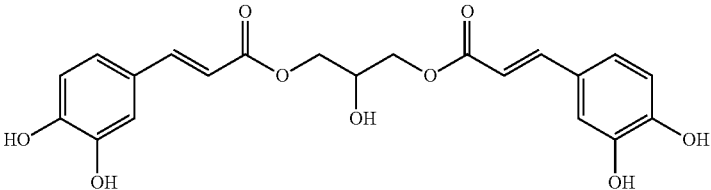 (IIb) | 71.2 | 38 |
| 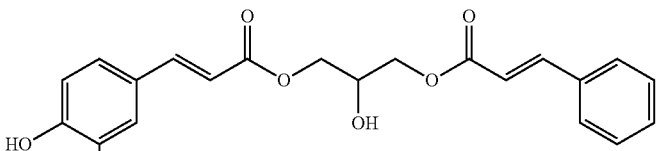 (Ie) | 37.0 | 23 |

TABLE 4-continued

Comparative Toxicity of compounds of the present invention in normal human fibroblast cells in-vitro (IC$_{50}$, μM)

| Compound | Inhibition Concentration (IC$_{50}$) μM | |
|---|---|---|
|  | GM9503 (Normal human fibroblast) | GM8399 (normal human fibroblast) |
| 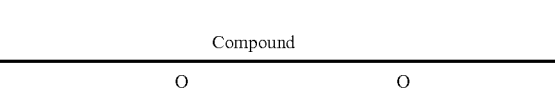 (Id) | 60.0 | 16 |

As shown above in Table 4, in normal human fibroblast cell lines, paclitaxel and caffeic acid are more toxic than compounds (IIb), (Ie) and (Id).

The therapeutic index for an anticancer compound compares the toxicity of the compound in a normal cell with an anti-proliferative effect in carcinoma cells. The index is a measure of the safety of the anticancer compound. The ratio of an IC$_{50}$ value in a normal human cell (e.g. a human fibroblast GM9503 cell) to an IC$_{50}$ value in a human carcinoma cell line for a particular anticancer compound provides comparative information on the safety and selectivity of the anticancer compound. The values of the therapeutic index shown in Table 5 demonstrate that the anticancer compounds (Ib), (Ie), and (Id) possess a larger therapeutic index and are therefore less toxic in comparison to paclitaxel (an approved anticancer drug). These results are significant since a successful anticancer therapy must not only demonstrate antitumor cytotoxicity but also show tolerable toxicity with respect to normal healthy cells.

TABLE 5

Values of therapeutic (safety) index* of anticancer compounds of the present invention

| Compound | A549 (Lung) | MCF-7 (Breast) | HCT116 (Colon) | PC-3 (Prostate) | SKOV-3 (Ovarian) |
|---|---|---|---|---|---|
| Taxol (Control) | 1.01 | 0.06 | 1.18 | 0.53 | 0.93 |
| 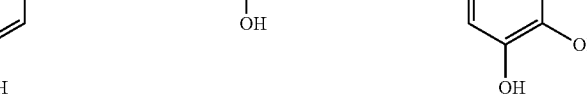 (IIb) | 3.38 | 0.95 | 2.63 | 10.52 | 4.51 |
| 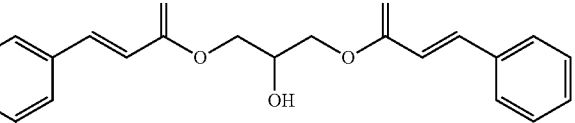 (Ie) | 1.12 | 1.13 | 1.34 | 4.14 | 2.26 |
| 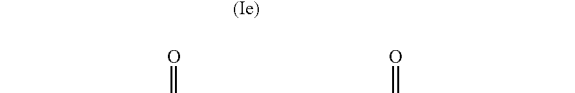 (Id) | 3.31 | 0.70 | 5.25 | 6.64 | 2.74 |

*Therapeutic index = toxicity (fibroblast)/anticancer inhibition = IC$_{50}$(GM9503)/IC$_{50}$ (carcinoma cell line)

Mechanism of Action

Human colon carcinoma cell line HCT116 was treated with compounds (I), (Ie) and (Id) and observed over a time period to determine the mechanism of cell death. The experiment was conducted as follows:

HCT116 cells were seeded and treated with each compound. At each time point, the cells were imaged using a neutral microscope at 63× magnification prior to fixing. The time points were 2, 4, 6, 8, 12, and 16 hours.

Cells treated with the compounds (IIb), (Ie) and (Id) exhibited the characteristic membrane blebbing morphology commonly seen during apoptosis (see FIGS. 12-15). Compound (IIb) appeared to be the most aggressive, followed by compound (Ie) and compound (Id). At 4 hr, a few cells in each well displayed membrane blebbing and a majority of the initial cellular population appeared to be undergoing apoptosis at the 6 hr and 8 hr time-points. At the 10 and 12 hr time-points, significantly fewer live cells were observed compared to the 2 and 4 hr time points, however, the cellular population appeared to slightly increase at 16 hrs. This may potentially be caused by a population doubling at this time-point.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

All patents, patent applications and publications cited in this application are hereby incorporated by reference in their entirety for all purposes to the same extent as if each individual patent, patent application and publication were so individually denoted.

REFERENCES (1) Jiang M C, Yang-Yen H F, Yen J J and Lin J K: Curcumin induces apoptosis in immortalized NIH 3T3 and malignant cancer cell lines. Nutr Cancer 26: 111-20, 1996.
(2) Kuo M L, Huang T S and Lin J K: Curcumin, an antioxidant and anti-tumor promoter, induces apoptosis in human leukemia cells. Biochim Biophys Acta 1317: 95-100, 1996.
(3) Mehta K, Pantazis P, McQueen T and Aggarwal B B: Antiproliferative effect of curcumin (diferuloylmethane) against human breast tumor cell lines, Anticancer Drugs 8: 470-81, 1997.
(4) Samaha H S, Kelloff G J, Steele V, Rao C V and Reddy B S: Modulation of apoptosis by sulindac, curcumin, phenylethyl-3-methylcaffeate, and 6-phenylhexyl isothiocyanate: apoptotic index as a biomarker in colon cancer chemoprevention and promotion. Cancer Res 57: 1301-5, 1997.
(5) Simon A, Allais D P, Duroux J L, Basly J P, Durand-Fontanier S and Delage C: Inhibitory effect of curcuminoids on MCF-7 cell proliferation and structure-activity relationships. Cancer Lett 129:111-6, 1998.
(6) Jee S H, Shen S C, Tseng C R, Chiu H C and Kuo M L: Curcumin induces a p53-dependent apoptosis in human basal cell carcinoma cells. J Invest Dermatol 111: 656-61, 1998.
(7) Mukhopadhyay A, Bueso-Ramos C, Chatterjee D, Pantazis P and Aggarwal B B: Curcumin downregulates cell survival mechanisms in human prostate cancer cell lines. Oncogene 20: 7597-609, 2001.
(8) Grunberger, D., Banerjee, R., Eisinger, K., Oltz. E. H., Efros, L., Caldwell, M.; Estevez, V., and Nakanishi, K. Preferential cytotoxicity on tumor cells by caffeic acid phenethyl ester isolated from propolis. Experientia. 44: 230-232, 1988.
(9) Su, Z-Z., Grunberger, D., and Fisher. P. B. Suppression of adenovirus type 5 E1A-mediated transformation and expression of the transformed phenotype by caffeic acid phenethyl ester (CAPE). Mol. Carcinogenesis. 4: 231-242, 1991.
(10) Guarini. L., Su. Z-z., Zucker, S., Lin, J., Grunberger, D. and Fisher. P. B. Growth inhibition and modulation of antigenic phenotype in human melanoma and glioblastoma multiforme cells by caffeic acid phenethyl ester (CAPE). Cell. Mol. Biol., 38:513-527, 1992.
(11) Rao, C. V., Desai, D., Kaul, B. Amin, S. and Reddy, B. S. Effect of caffeic acid esters on carcinogen-induced mutagenicity and human colon adenocarcinoma cell growth. Chem.-Biol. Interact., 84: 277-290, 1992.
(12) Rao, C. V., Desai, D., Simi, B., Kulkarni, N., Amin, S., and Reddy, B. S. Inhibitory effect of caffeic acid esters on azoxymethane-induced biochemical changes and aberrant crypt foci formation in rat colon. Cancer Res. 53: 4182-4188. 1993.
(13) Frankel. K. Wei, H. Bhimani, R. Zadunaisky, J. A., Ferrara, T. Huang, M. T., Conney, A. H., and Grunberger, D. Inhibition of tumor promoter-mediated processes in mouse skin and bovine lens by caffeic acid phenethyl ester. Cancer Res., 53:1255-1261, 1993.

What is claimed is:

1. A method for inducing apoptosis of cancer cells in a subject, comprising: administering to a subject in need thereof an effective amount of a compound of formula (Ia) or (Ia'):

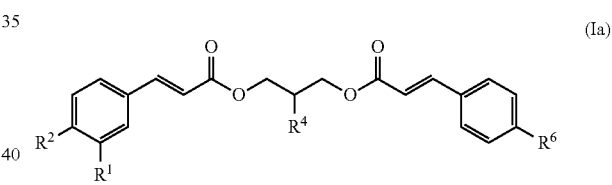

(Ia)

wherein:
$R^1$ and $R^2$ are independently OH, alkoxy or alkylcarbonyloxy,
$R^4$ is OH, and
$R^6$ is H, alkoxy or alkylcarbonyloxy,
or a pharmaceutically acceptable salt thereof.

2. A method for inducing apoptosis of cancer cells in a subject, comprising: administering to a subject in need thereof an effective amount of a compound of formula (Ic) or (Ic'):

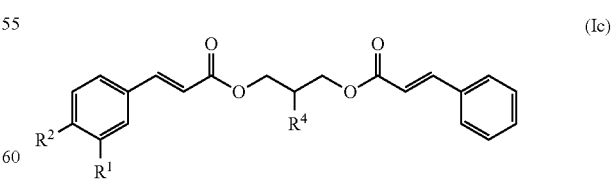

(Ic)

wherein:
$R^1$ and $R^2$ are independently OH, alkoxy or alkylcarbonyloxy,
$R^4$ is OH, and
or a pharmaceutically acceptable salt thereof.

3. A method for inducing apoptosis of cancer cells in a subject, comprising: administering to a subject in need thereof an effective amount of a compound of formula (II) or (II'):

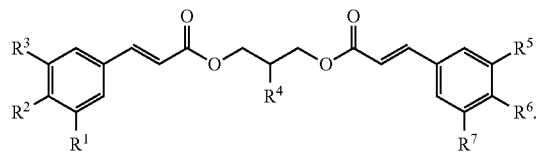
(II)

wherein $R^4$ is OH, $R^1$ and $R^2$ are both OH or both alkoxy, $R^6$ and $R^7$ are independently H, OH, alkoxy or alkylcarbonyloxy, or a pharmaceutically acceptable salt thereof, provided that the compound is other than (2E,2'E)-2-acetoxypropane-1,3-diyl bis(3-(4-hydroxyphenyl)acrylate) and (E)-2-acetoxy-3-(((E)-3-(4-hydroxy-3-methoxyphenyl)acryloyl)oxy)propyl 3-(4-hydroxyphenyl)acrylate.

4. The method according to claim 3, wherein $R^1$ and $R^2$ are both OH.

5. The method according to claim 1, wherein $R^6$ is H.

6. The method according to claim 3, wherein $R^1$ and $R^2$ are both alkoxy.

7. The method according to claim 6, wherein $R^3$ is H.

8. A method for inducing apoptosis of cancer cells in a subject, comprising: administering to a subject in need thereof an effective amount of a compound of the formula (Id) or (Id'):

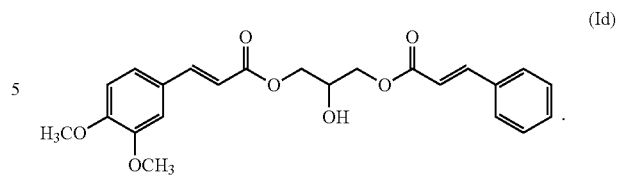
(Id)

9. A method for inducing apoptosis of cancer cells in a subject, comprising: administering to a subject in need thereof an effective amount of a compound of formula (Ie) or (Ie'):

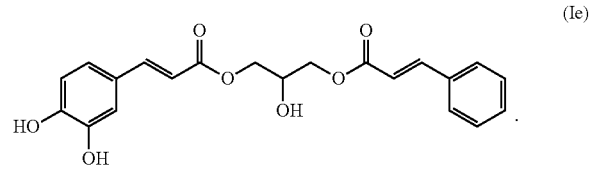 [SMILES: O=C(/C=C/c1ccccc1)OCC(O)COC(=O)/C=C/c1ccc(O)c(O)c1]
(Ie)

10. A method for inducing apoptosis of cancer cells in a subject, comprising: administering to a subject in need thereof an effective amount of a compound of formula (If) or (If'):

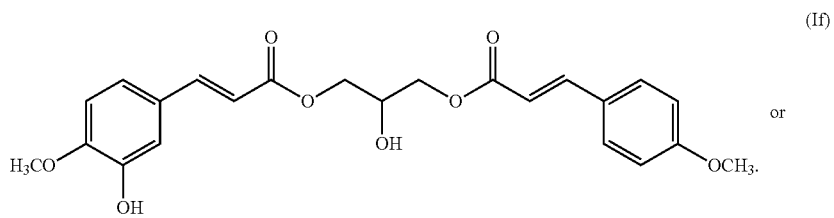 [SMILES: COc1ccc(/C=C/C(=O)OCC(O)COC(=O)/C=C/c2ccc(OC)c(O)c2)cc1]
(If)

11. A method for inducing apoptosis of cancer cells in a subject, comprising: administering to a subject in need thereof an effective amount of a compound formula (Ig) or (Ig'):

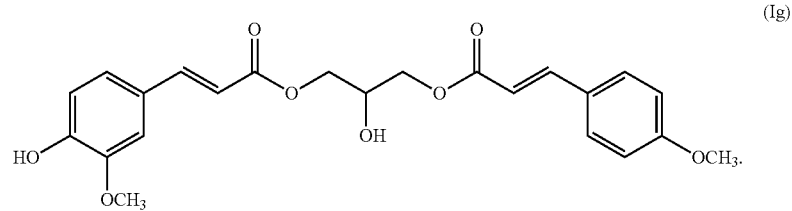 [SMILES: COc1ccc(/C=C/C(=O)OCC(O)COC(=O)/C=C/c2ccc(O)c(OC)c2)cc1]
(Ig)

12. A method for inducing apoptosis of cancer cells in a subject, comprising: administering to a subject in need thereof an effective amount of a compound formula (IIb) or (IIb'):

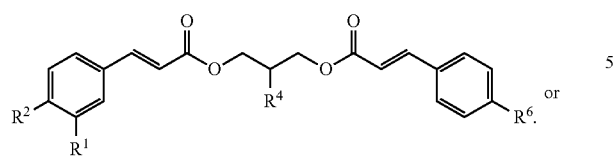
(Ia)
13. A method for inducing apoptosis of cancer cells in a subject, comprising: administering to a subject in need thereof an effective amount of a compound formula (IIc) or (IIc'):
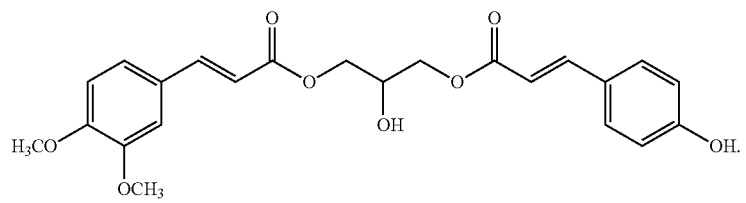
(IIc)
* * * * *